US 7,377,938 B2

(12) United States Patent
Sarac et al.

(10) Patent No.: US 7,377,938 B2
(45) Date of Patent: May 27, 2008

(54) PROSTHETIC CARDIAC VALUE AND METHOD FOR MAKING SAME

(75) Inventors: Timur Paul Sarac, Orange Village, OH (US); Nicholas G. Smedira, Moreland Hills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 377 days.

(21) Appl. No.: 10/880,277

(22) Filed: Jun. 29, 2004

(65) Prior Publication Data

US 2004/0236411 A1 Nov. 25, 2004

Related U.S. Application Data

(60) Continuation-in-part of application No. 10/409,884, filed on Apr. 9, 2003, now Pat. No. 7,137,947, which is a division of application No. 09/908,764, filed on Jul. 19, 2001, now Pat. No. 6,579,307.

(51) Int. Cl.
*A61F 2/06* (2006.01)
*A61F 2/24* (2006.01)

(52) U.S. Cl. ..................................... 623/1.26

(58) Field of Classification Search ...... 623/1.24–1.26, 623/2.11–2.12, 2.14, 2.18
See application file for complete search history.

(56) References Cited

U.S. PATENT DOCUMENTS

| 4,666,442 A | 5/1987 | Arru et al. |
| 4,681,588 A | 7/1987 | Ketharanathan |
| 4,755,593 A | 7/1988 | Lauren |
| 4,969,896 A | 11/1990 | Shors |
| 5,192,311 A | 3/1993 | King et al. |
| 5,489,297 A | 2/1996 | Duran |
| 5,500,014 A | 3/1996 | Quijano et al. |
| 5,549,666 A | 8/1996 | Hata et al. |
| 5,562,727 A | 10/1996 | Turk et al. |
| 5,667,523 A | 9/1997 | Bynon et al. |
| 5,693,085 A | 12/1997 | Buirge et al. |
| 5,840,081 A * | 11/1998 | Andersen et al. .......... 623/1.11 |
| 5,865,723 A | 2/1999 | Love |

(Continued)

FOREIGN PATENT DOCUMENTS

WO WO 97/09006 A1 3/1997

(Continued)

OTHER PUBLICATIONS

Sarac et al. "In vivo and mechanical properties of peritoneum/fascia as a novel arterial substitute." Journal of Vascular Surgery, 2004; 41:490-497.

*Primary Examiner*—Alvin J. Stewart
(74) *Attorney, Agent, or Firm*—Tarolli, Sundheim, Covell & Tummino LLP

(57) ABSTRACT

A prosthetic valve for replacing a cardiac valve includes an expandable support member and at least two valve leaflets made of a first layer of biological material selected from peritoneal tissue, pleural tissue or pericardial tissue. A second layer of biological material is attached to the support member. The second layer is also made from peritoneal tissue, pleural tissue or pericardial tissue. The second layer includes a radially inwardly facing surface that defines a conduit for directing blood flow. The valve leaflets extend across the conduit to permit unidirectional flow of blood through the conduit. Methods for making and implanting the prosthetic valve are also provided.

6 Claims, 13 Drawing Sheets

U.S. PATENT DOCUMENTS

| | | |
|---|---|---|
| 5,876,432 A | 3/1999 | Lau et al. |
| 5,891,193 A | 4/1999 | Robinson et al. |
| 6,077,217 A | 6/2000 | Love et al. |
| 6,245,100 B1 | 6/2001 | Davila et al. |
| 6,254,564 B1 * | 7/2001 | Wilk et al. ............... 604/9 |
| 6,287,334 B1 | 9/2001 | Moll et al. |
| 6,299,637 B1 | 10/2001 | Shaolian et al. |
| 6,331,191 B1 | 12/2001 | Chobotov |
| 6,355,055 B1 | 3/2002 | Waksman et al. |
| 6,358,275 B1 | 3/2002 | McIlroy et al. |
| 6,440,164 B1 * | 8/2002 | DiMatteo et al. ......... 623/1.24 |
| 6,458,153 B1 * | 10/2002 | Bailey et al. ............ 623/1.24 |
| 6,494,909 B2 | 12/2002 | Greenhalgh |
| 6,503,272 B2 | 1/2003 | Duerig et al. |
| 6,579,307 B2 | 6/2003 | Sarac |
| 6,582,462 B1 | 6/2003 | Andersen et al. |
| 6,605,112 B1 | 8/2003 | Moll et al. |
| 7,128,759 B2 * | 10/2006 | Osborne et al. ........... 623/1.24 |
| 2003/0149477 A * | 8/2000 | Gabbay .................. 623/2.14 |
| 2002/0138137 A1 | 9/2002 | Cox |
| 2002/0143393 A1 | 10/2002 | Cox |
| 2003/0023303 A1 | 1/2003 | Palmaz et al. |
| 2003/0195608 A1 | 10/2003 | Sarac |
| 2003/0199971 A1 * | 10/2003 | Tower et al. .............. 623/1.24 |
| 2004/0093070 A1 | 5/2004 | Hojeibane et al. |
| 2005/0137681 A1 * | 6/2005 | Shoemaker et al. ....... 623/1.23 |
| 2005/0137682 A1 * | 6/2005 | Justino .................. 623/1.24 |

FOREIGN PATENT DOCUMENTS

| | | |
|---|---|---|
| WO | WO 02/47575 A2 | 6/2002 |
| WO | WO 02/076349 A1 | 10/2002 |
| WO | WO 03/071990 A1 | 9/2003 |

* cited by examiner

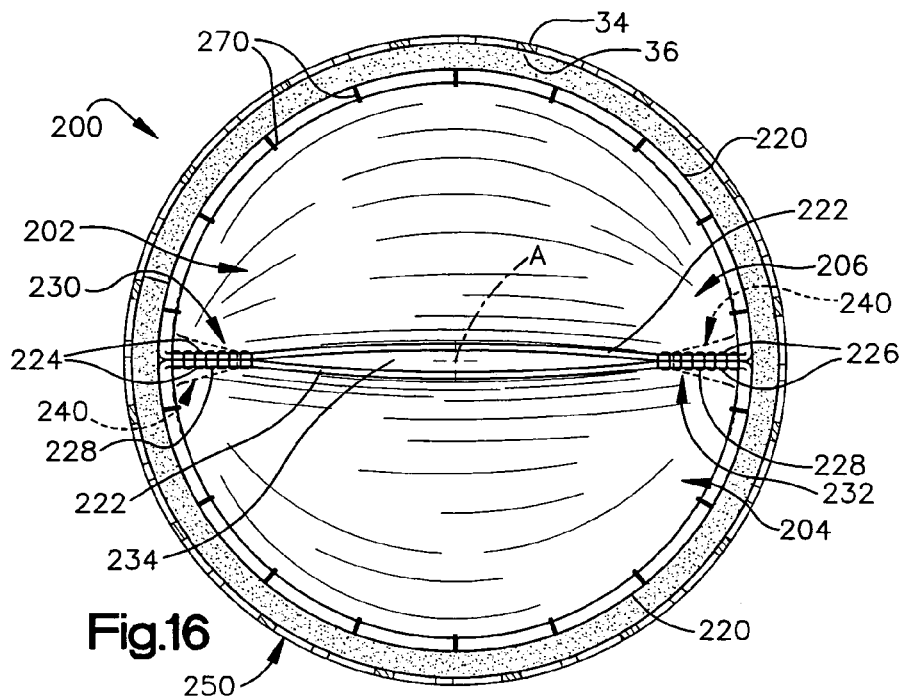
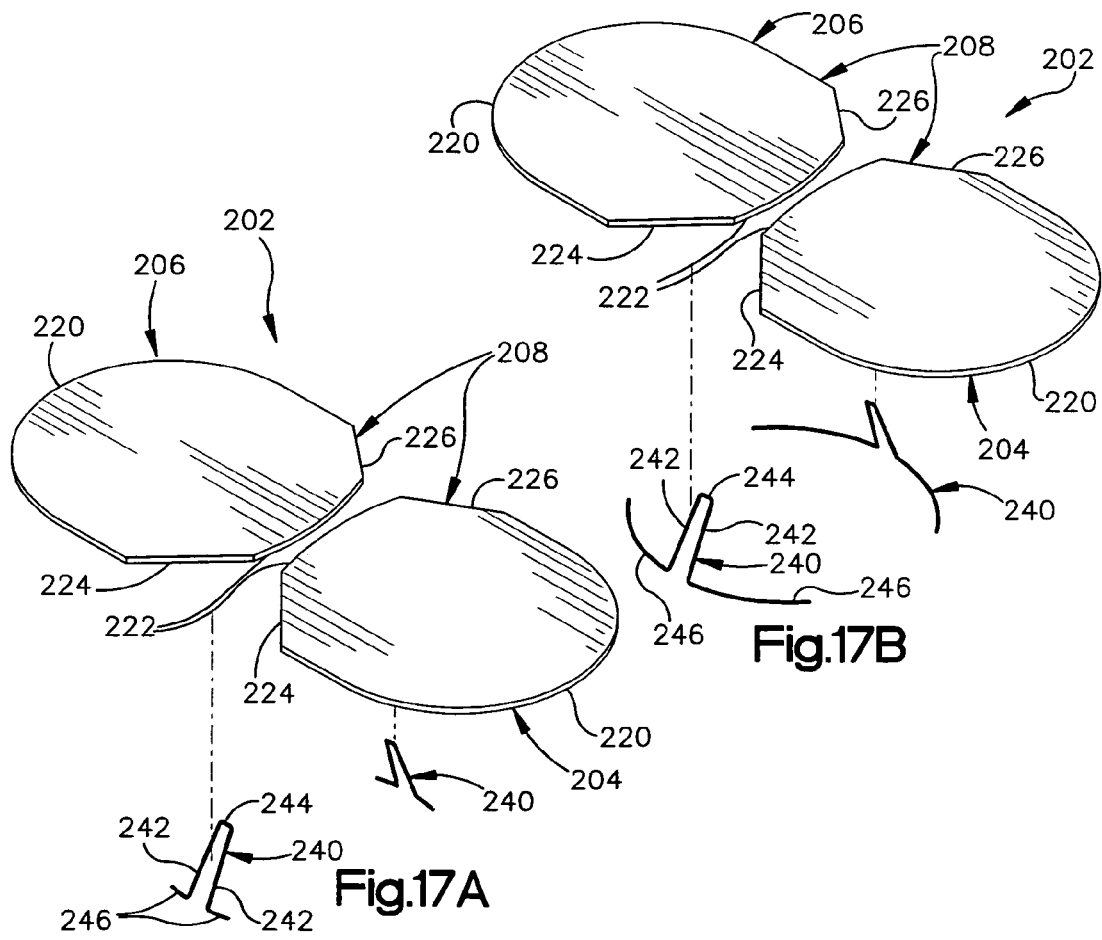

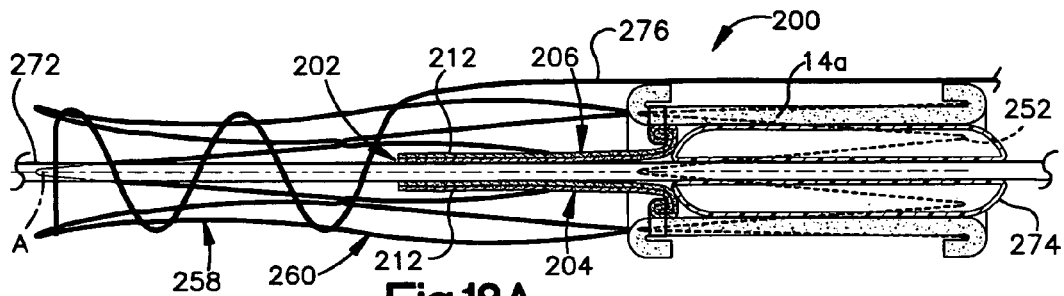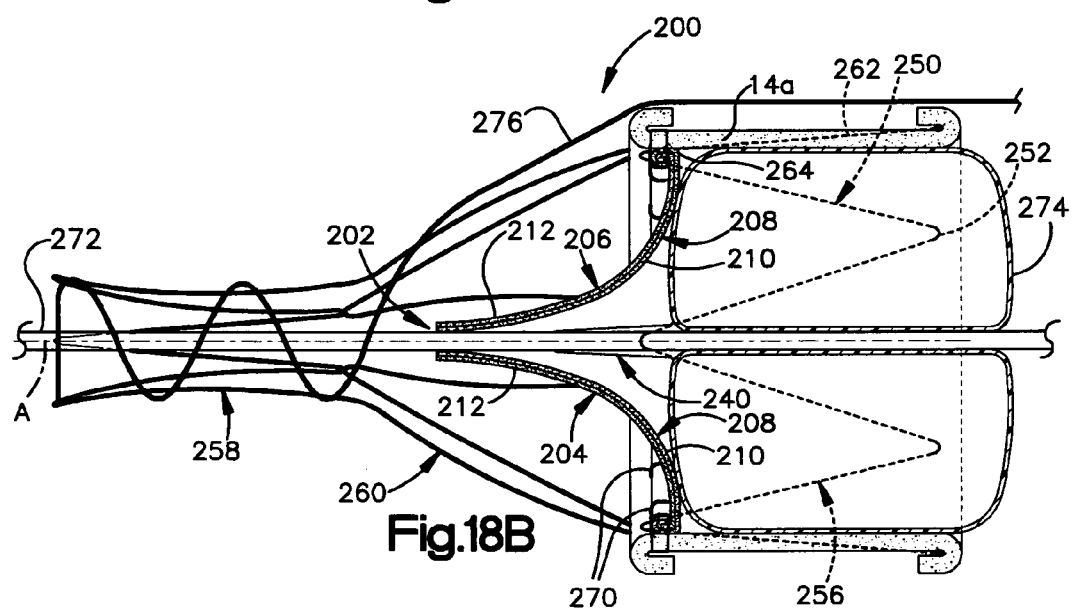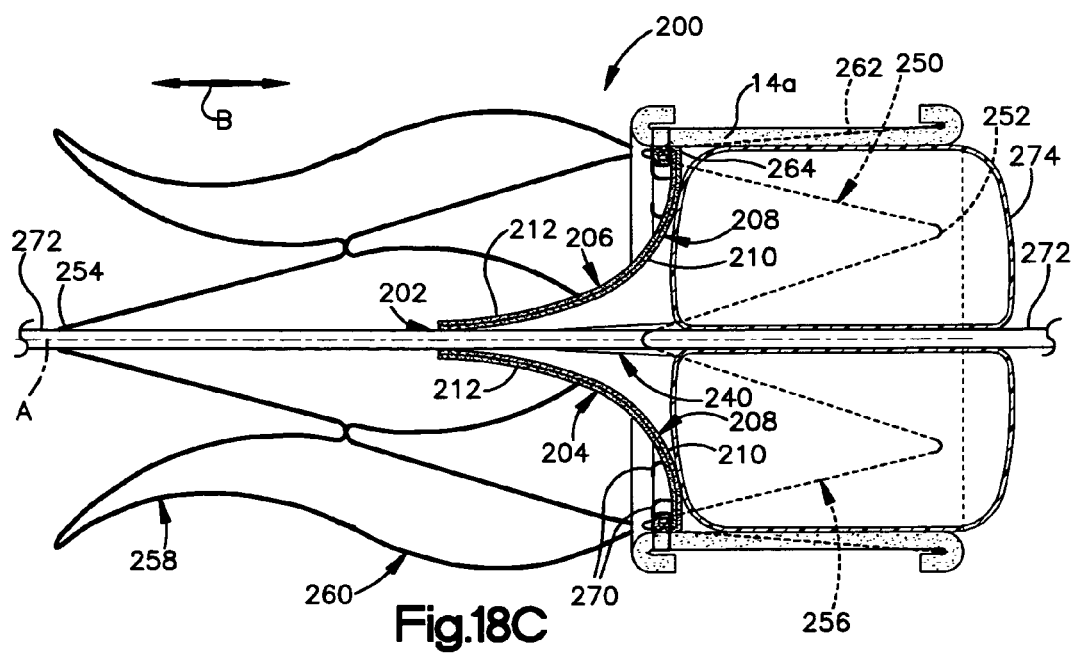

PROSTHETIC CARDIAC VALUE AND METHOD FOR MAKING SAME

RELATED APPLICATIONS

This application is a continuation-in-part application U.S. patent application Ser. No. 10/409,884, filed Apr. 9, 2003 now U.S. Pat. No. 7,137,947, which is a divisional application of Ser. No. 09/908,764 now U.S. Pat. No. 6,579,307, filed Jul. 19, 2001 and issued Jun. 17, 2003, both of which are assigned to the assignee of the present invention and are incorporated herein by reference.

TECHNICAL FIELD

The present invention relates to a prosthetic cardiac valve and methods for making and implanting the prosthetic valve.

BACKGROUND OF THE INVENTION

Surgical procedures in which a cardiovascular prosthesis is implanted into a patient's blood vessel are common in treating many vascular disorders. For example, one common type of cardiovascular prosthesis is an endovascular prosthesis that is used to strengthen a blood vessel wall in the location of an aneurysm, or to open an occlusion in a blood vessel.

A typical endovascular prosthesis includes a flexible, tubular member, made of fabric or PTFE, that may be anchored with sutures or carried by one or more support structures known as stents. Generally, each stent is formed from a material having an elasticity that is sufficient to permit radial expansion of the stent and having a strength sufficient to prevent radial collapse or burst. Such stents are typically formed from stainless steel, titanium, Nitinol, or a suitable plastic.

A common endeavor in the field of cardiovascular prosthetics is to increase the patency rate of prostheses. Thrombosis and platelet deposition on surfaces of a cardiovascular prosthesis reduce the patency rate of the prosthesis. For example, thrombosis and platelet deposition within an endovascular prosthesis may occlude the conduit defined by the endovascular prosthesis.

Many factors contribute to thrombosis and platelet deposition on the surfaces of known cardiovascular prosthesis. The most common factors are dependent upon the material or materials forming the inner surface of the conduit of the endovascular prosthesis. Typically, thrombosis and platelet deposition begin to occlude the conduit of the endovascular prosthesis when the material or materials forming the conduit of the endovascular prosthesis are foreign to the patient's body. Thrombus begins to form on the inner surface of the conduit of the endovascular prosthesis and extends annularly about the inner surface of the conduit. Eventually, the thrombus can severely restrict blood flow through the conduit defined by the endovascular prosthesis and, if left untreated, can completely occlude the conduit.

Additionally, thrombosis and platelet deposition may occur as a result of irregularities on the inner surface of a cardiovascular prosthesis. The irregularities may be formed by the structure of an inner stent that is used to support the cardiovascular prosthesis, or may be formed by the inner surface of the flexible member used for the prosthesis.

Another common type of cardiovascular prosthesis is a prosthetic cardiac valve. Prosthetic cardiac valves have been used to replace all four of the native cardiac valves. Cardiac valve replacement has traditionally been done though an invasive open surgical procedure, although percutaneous approaches are being developed.

The four native cardiac valves (mitral, aortic, tricuspid, and pulmonary) serve to direct the flow of blood through the two sides of the heart in a forward direction. On the left (systemic) side of the heart, the mitral valve is located between the left atrium and the left ventricle, while the aortic valve is located between the left ventricle and the aorta. These two valves direct oxygenated blood coming from the lungs, through the left side of the heart, into the aorta for distribution to the body. On the right (pulmonary) side of the heart, the tricuspid valve is located between the right atrium and the right ventricle, while the pulmonary valve is located between the right ventricle and the pulmonary artery. These two valves direct de-oxygenated blood coming from the body, through the right side of the heart, into the pulmonary artery for distribution to the lungs, where it again becomes re-oxygenated to begin the circuit anew.

All four of these native heart valves are passive structures that do not themselves expend any energy and do not perform any active contractile function. The valves consist of moveable leaflets that open and close in response to differential pressures on either side of the valve. The mitral and tricuspid valves are referred to as atrioventricular valves because they are situated between an atrium and a ventricle on each side of the heart. The mitral valve has two leaflets and the tricuspid valve has three leaflets. The aortic and pulmonary valves are referred to as semilunar valves because of the unique appearance of their leaflets, which are often termed "cusps" and which are shaped somewhat like a half-moon. The aortic and pulmonary valves each have three cusps.

Heart valves can exhibit abnormal anatomy and function as a result of congenital or acquired valve disease. Congenital valve abnormalities may be so severe that emergency surgery is required within the first few hours of life, or they may be well-tolerated for many years only to develop a life-threatening problem in an elderly patient. Acquired valve disease may result from causes such as rheumatic fever, degenerative disorders of the valve tissue, bacterial or fungal infections, and trauma.

The two major problems that can develop with heart valves are stenosis, in which a valve does not open properly, and insufficiency (also called regurgitation), in which a valve does not close properly. Stenosis and insufficiency may occur concomitantly in the same valve or in different valves. Both of these abnormalities increase the workload and stress placed on the heart. The severity of this increased stress on the heart, and the heart's ability to adapt to it, determine whether the abnormal valve will have to be surgically repaired or replaced.

In addition to stenosis and insufficiency of heart valves, surgery may also be required for certain types of bacterial or fungal infections in which the valve may continue to function normally, but nevertheless harbors an overgrowth of bacteria on the leaflets of the valve that may flake off (or embolize) and lodge downstream in a vital artery. If this occurs on the valves of the left side (i.e., the systemic circulation side) of the heart, embolization results in sudden loss of the blood supply to the affected body organ and immediate malfunction of that organ. The organ most commonly affected by such embolization is the brain, in which case the patient suffers a stroke. Thus, surgical replacement of either the mitral or the aortic valve may be necessary for this problem even though neither stenosis nor insufficiency of either valve is present.

If a heart valve must be replaced, there are currently several options available, and the choice of a particular type of prosthesis (i.e., artificial valve) depends on factors such as the location of the valve, the age and other specifics of the patient, and the surgeon's experiences and preferences. Available prostheses include mechanical valves, tissue valves, and homograft valves. Mechanical valves include caged-ball valves, bi-leaflet valves, and tilting disk valves. The main advantage of mechanical valves is their long-term durability. Their main disadvantage is that they require the patient to take systemic anticoagulation drugs for the rest of his or her life, because of the propensity of mechanical valves to cause blood clots to form on them. Mechanical valves can be used to replace any of the heart's four valves and are typically attached to a fabric sewing ring so that the valve prosthesis can be sutured to the patient's native tissue to hold the artificial valve in place postoperatively.

Tissue valves are typically constructed either by sewing the leaflets of porcine aortic valves to a stent (to hold the leaflets in proper position), or by constructing valve leaflets from porcine or bovine pericardial tissue and sewing them to a stent. The stents may be rigid or slightly flexible and are typically covered with a fabric, such as the material sold under the trademark DACRON™, and then attached to a sewing ring for fixation to the patient's native valve annulus. The porcine or bovine tissue is chemically treated to alleviate any antigenicity (i.e., to reduce the risk that the patient's body will reject the foreign tissue). Tissue valves may be used to replace any of the heart's four valves. The main advantage of tissue valves is that they do not cause blood clots to form as readily as do the mechanical valves, and therefore, they do not absolutely require systemic anticoagulation. Nevertheless, many surgeons do anticoagulate patients who have any type of artificial mitral valve, including tissue valves. The major disadvantage of tissue valves is that they lack the long-term durability of mechanical valves.

It should be noted that the structure associated with mechanical valves and tissue valves decreases their hemodynamic performance. Such obstructions also interfere with the normal flow patterns within and around the prosthetic valve and therefore, promote thrombosis as all artificial surfaces are thrombogenic (clot-promoting) to a greater or lesser degree.

Homograft valves are harvested from human cadavers. Homograft valves are most commonly implanted in the aortic position, but are also occasionally implanted in the pulmonary position. Homograft valves are specially prepared and frozen in liquid nitrogen, where they are stored for later use. The advantage of aortic homograft valves is that they appear to be as durable as mechanical valves, but do not promote blood clot formation and therefore do not require anticoagulation. The main disadvantage of these valves is that they are not available in sufficient numbers to satisfy the needs of patients who need new aortic or pulmonary valves. Homograft valves are also extremely expensive and can be more difficult to implant than either mechanical valves or tissue valves.

SUMMARY OF THE INVENTION

The present invention is a prosthetic valve for replacing a cardiac valve. The prosthetic valve comprises an expandable support member and at least two valve leaflets made of a first layer of biological material selected from a group consisting of peritoneal tissue, pleural tissue and pericardial tissue. A second layer of biological material is attached to the support member. The second layer is selected from a group consisting of peritoneal tissue, pleural tissue and pericardial tissue. The second layer includes a radially inwardly facing surface that defines a conduit for directing blood flow. The at least two valve leaflets extend across the conduit to permit unidirectional flow of blood through the conduit.

In accordance with one aspect of the invention, the support member comprises a stent having inner and outer surfaces, the second layer being attached to the inner surface.

In accordance with another aspect of the invention, the support means further comprises a strut member located at each of at least two commissural sides formed by the junctions of adjoining portions of the at least two valve leaflets.

In accordance with another aspect of the invention, the second layer extends along a portion of the length of the stent to form an enclosed section of the stent that is lined with the second layer and at least one bare section of the stent that is not lined with the second layer.

In accordance with another aspect of the invention, the stent has oppositely disposed proximal and distal end sections and a center section disposed between the end sections. The at least two valve leaflets extend within the center section.

In accordance with another aspect of the invention, the second layer extends along the center section of the stent.

In accordance with another aspect of the invention, the second layer includes at least two radial openings in the center section.

In accordance with another aspect of the invention, the second layer further extends along the proximal end section of the stent.

In accordance with another aspect of the invention, the proximal and distal end sections of the stent are bare and the center section of the stent is lined with the second layer.

In accordance with another aspect of the invention, the center section of the stent has a convex shape in the axial direction for conforming to the shape of the cardiac wall downstream of the cardiac valve.

In accordance with another aspect of the invention, the distal end section of the stent has a concave shape in the axial direction for conforming to the shape of the cardiac wall downstream of the cardiac valve.

In accordance with another aspect of the invention, the second layer of biological material comprises a serous membrane.

In accordance with another aspect of the invention, the first layer of biological material comprises a serous membrane.

In accordance with another aspect of the invention, the first layer of biological material comprises an inner lining of a serous membrane and an outer lining of fascia.

In accordance with another aspect of the invention, each of the at least two valve leaflets has an oppositely disposed pair of lateral sides spaced apart by a free edge. The lateral sides of each of the at least two valve leaflets adjoin each other and are attached to each other to form at least two commissural sides that are separated by the free edges. The free edges are coaptable to permit unidirectional flow of blood through the conduit.

In accordance with another aspect of the invention, the support means comprises at least one strut member positioned at each of the commissural sides formed at the junction of the lateral sides of the at least two valve leaflets.

The present invention further provides a prosthetic valve for replacing an aortic valve. The prosthetic valve comprises an expandable stent having inner and outer surfaces, and at least two valve leaflets made of a first layer of biological material selected from a group consisting of peritoneal tissue, pleural tissue and pericardial tissue. A second layer of biological material is attached to the inner surface of the stent. The second layer is selected from a group consisting of peritoneal tissue, pleural tissue and pericardial tissue. The second layer includes a radially inwardly facing surface that defines a conduit for directing blood flow. The at least two valve leaflets extend across the conduit to permit unidirectional flow of blood through the conduit.

The present invention also provides a method for producing a prosthetic valve. According to the inventive method, a first layer of biological material comprising a single sheet of material selected from a group consisting of peritoneal tissue, pleural tissue and pericardial tissue is harvested. The sheet of biological material is trimmed to form at least two valve leaflets. Each of the at least two valve leaflets has an oppositely disposed pair of lateral sides spaced apart by a free edge. The lateral sides of each of the at least two valve leaflets are placed adjacent each other and attached to each other to form an oppositely disposed pair of commissural sides separated by the free edges that are coaptable to permit unidirectional flow of blood. The sheet of biological material is attached to an expandable stent to provide structural support for the at least two valve leaflets. A second layer of biological material selected from a group consisting of peritoneal tissue, pleural tissue and pericardial tissue is harvested. The second layer of biological material is attached to an inner surface of the stent.

The present invention also provides a method for replacing a cardiac valve with a prosthetic valve. According to the inventive method, a first layer of biological material comprising a single sheet of material selected from a group consisting of peritoneal tissue, pleural tissue and pericardial tissue is harvested. The sheet of biological material is trimmed to form at least two valve leaflets. Each of the at least two valve leaflets has an oppositely disposed pair of lateral sides spaced apart by a free edge. The lateral sides of each of the at least two valve leaflets are placed adjacent each other and attached to each other to form an oppositely disposed pair of commissural sides separated by the free edges that are coaptable to permit unidirectional flow of blood. The sheet of biological material is attached to an expandable stent to provide structural support for the at least two valve leaflets. The support means comprises an expandable stent having oppositely disposed proximal and distal end sections and a center section disposed between the end sections. The at least two valve leaflets are attached to the center section of the stent. A second layer of biological material selected from a group consisting of peritoneal tissue, pleural tissue and pericardial tissue is harvested. The second layer of biological material is attached to an inner surface of the stent to complete the process of forming the prosthetic valve. The stent is then collapsed into a radially compressed condition. The prosthetic valve is inserted into the heart to the annulus of the cardiac valve in the compressed condition and is subsequently expanded into engagement with the annulus.

In accordance with another aspect of the inventive method, at least one of the proximal, distal, and center sections of the stent is expanded with an inflatable balloon.

In accordance with another aspect of the inventive method, at least one of the proximal, distal, and center sections of the stent self-expands.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 16 is an end view taken along line 16-16 in FIG. 15;

FIG. 17A is a perspective view of certain components of the apparatus of FIGS. 14-16;

FIG. 17B is a view similar to FIG. 17A illustrating an alternate construction for the components shown in FIG. 17A;

FIG. 18A is a schematic sectional view illustrating the apparatus of FIG. 14 in a collapsed condition and loaded on an inflatable balloon catheter prior to implantation in the aortic position;

FIG. 18B is a schematic sectional view similar to FIG. 18A illustrating the apparatus in a partially expanded condition;

FIG. 18C is a schematic sectional view similar to FIG. 18C illustrating the apparatus in a fully expanded condition

DETAILED DESCRIPTION OF EMBODIMENTS

Figure 1:
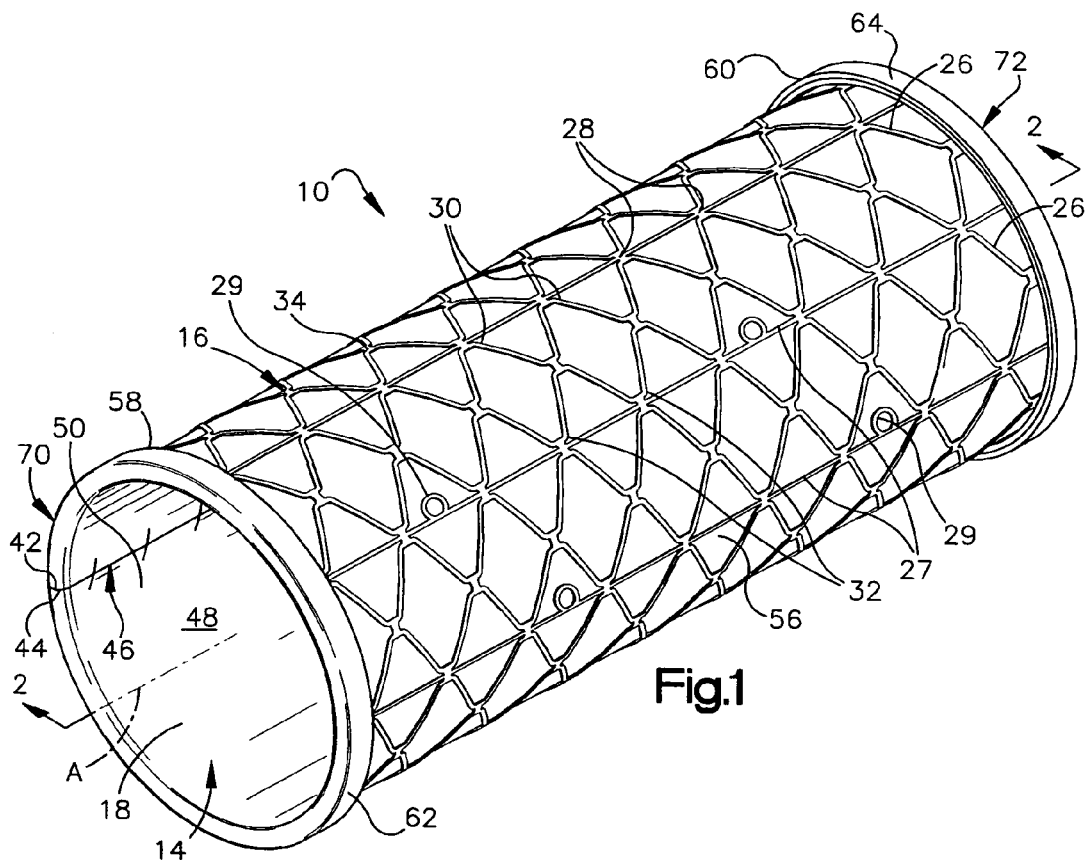
FIG. 1 is a perspective view of an apparatus constructed in accordance with the present invention.
Figure 5:
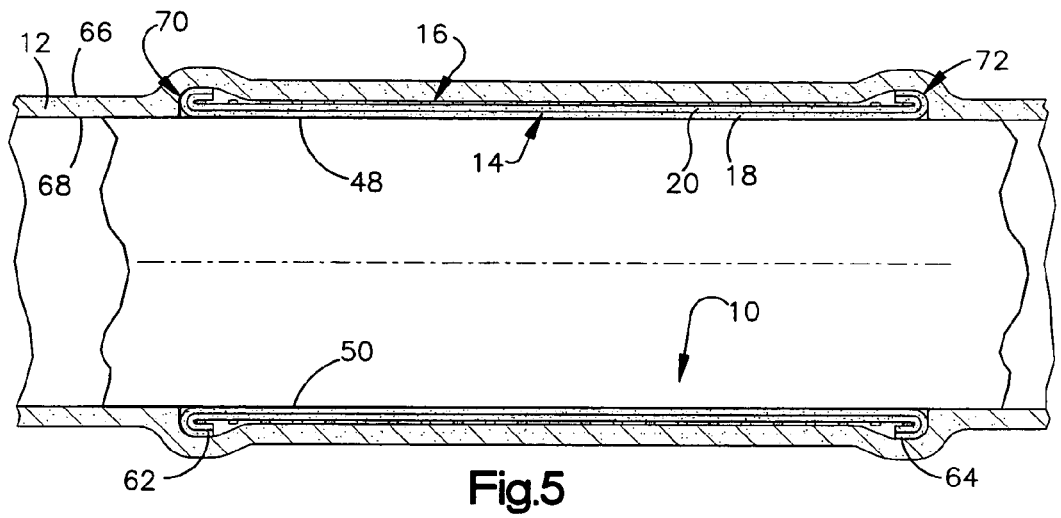
FIG. 5 is a sectional view illustrating the apparatus of FIG. 1 implanted in a blood vessel.

FIG. 1 is a perspective view of an apparatus 10 that is constructed in accordance with the present invention. The apparatus 10 is a cardiovascular graft for grafting of a blood vessel 12 (FIG. 5). The apparatus 10 includes a layer of biological tissue 14 and an expandable support member 16 or stent.

Figure 2:
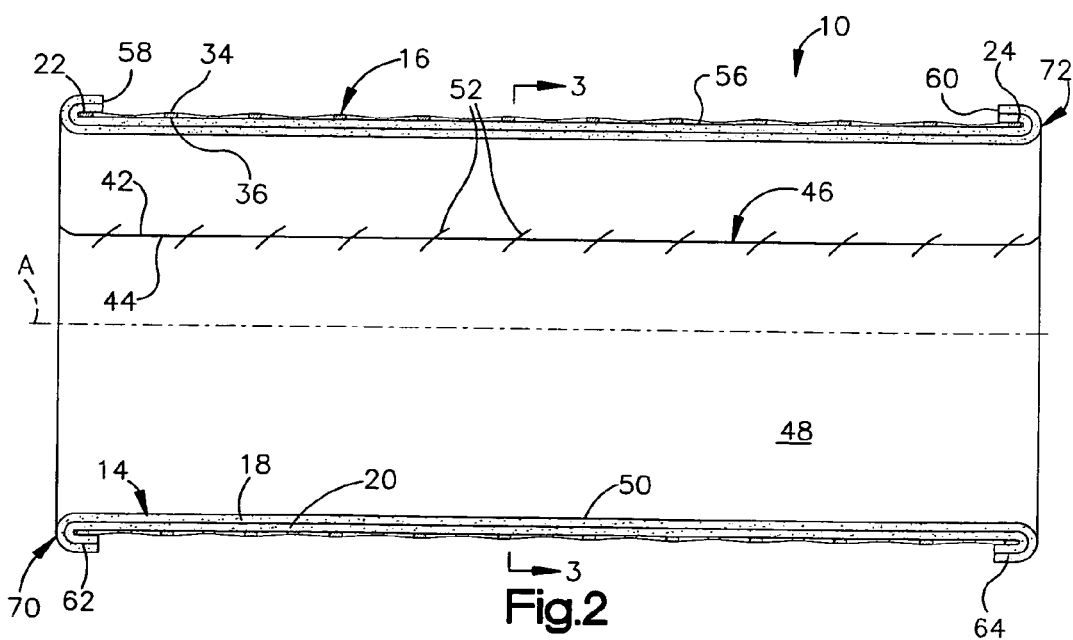
FIG. 2 is a view along line 2-2 in FIG. 1.
Figure 3:
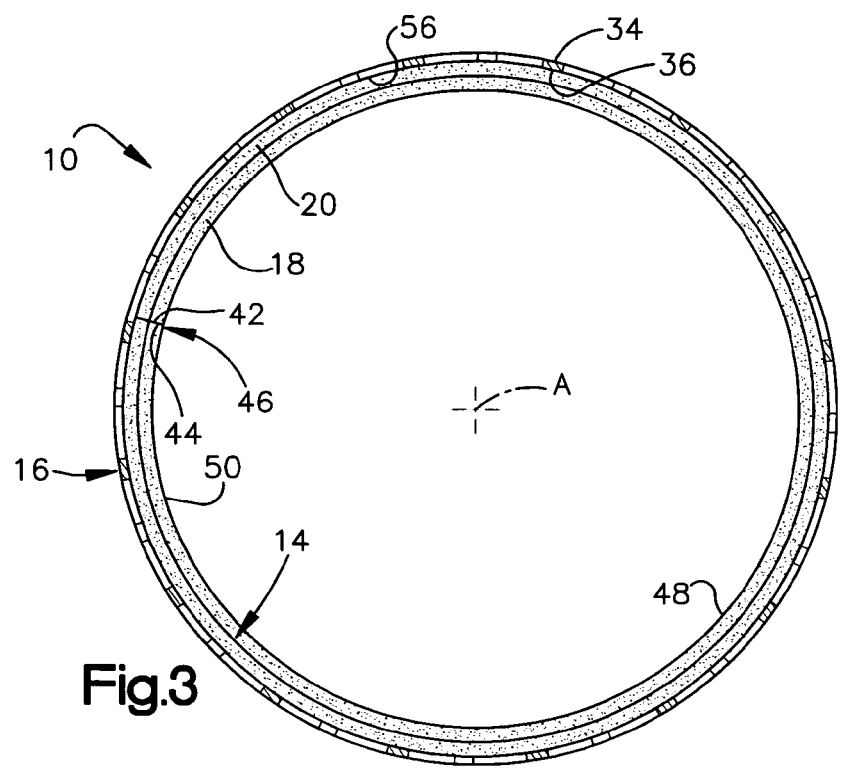
FIG. 3 is a view along line 3-3 in FIG. 2.

The layer of biological tissue 14 includes an inner lining 18 and an outer lining 20 (FIGS. 2 and 3). The inner lining 18 is a serous membrane and the outer lining 20 is fascia associated with the serous membrane. The biological tissue 14 is autogenous tissue. Alternatively, cadaveric tissue or xenogeneic tissue may be used. According to one embodiment, the layer of biological tissue 14 is harvested peritoneal fascia tissue. Alternatively, the biological tissue may be harvested pleural tissue or harvested pericardial tissue.

The biological tissue 14 is harvested in sheets of appropriate size. Conventional techniques are used for harvesting the biological tissue 14. The sheet of biological tissue 14 is fixed or preserved with alcohol, glutaraldehyde, and/or another biological solution. After being fixed, the biological tissue 14 is trimmed or cut into the desired shape and size. It is noted that the biological tissue 14 may shrink slightly when fixed. Thus, the biological tissue 14 should be fixed prior to being trimmed to the desired shape and size. Preferably, the biological tissue 14 is trimmed into a rectangular shape. After being trimmed, the biological tissue may be bathed in the biological solution.

The expandable support member 16 is tubular and extends axially from a first end 22 (FIG. 2) to a second end 24. The expandable support member 16 illustrated in FIG. 1 is a mesh structure that includes a plurality of support beams 26 and a plurality of axially extending support rods 27.

Each support beam 26 has a generally sinusoidal shape. The wavelength of each of the support beams 26 is identical or nearly identical to the wavelength of adjacent support beams. Circumferentially adjacent support beams 26 are 180° out of phase from one another. Connector bars 28 (FIG. 1) connect the peaks 30 of each support beam 26 to the associated troughs 32 (FIG. 1) of the adjacent support beam. The amplitude (or height) of each support beam 26 is designed so that a whole number of support beams forms the circumference of the expandable support member 16.

Each of the axially extending support rods 27 extends parallel to axis A. The support rods 27 add additional support to the expandable support member 16. One embodiment of the apparatus 10 includes eight support rods 27 that are equally spaced about the circumference of the expandable support member 16. In the embodiment illustrated in FIG. 1, two support beams 26 are located between adjacent support rods 27.

The expandable support member 16 also includes a plurality of eyelets 29, four of which are shown in FIG. 1. Each eyelet 29 extends from one of the support rods 27. The eyelets 29 illustrated in FIG. 1 are circular, however other shapes may be used. The eyelets 29 provide a means for suturing the layer of biological tissue 14 to the outer support member 16.

The expandable support member 16 is formed from an expandable metal, such as Nitinol. Alternatively, the expandable support may be formed from a fabric layer such as Dacron® or a plastic material such as polytetraflouroethylene (PTFE).

The expandable support member 16 includes an outer surface 34 and an inner surface 36 (FIG. 2). The outer surface 34 is generally cylindrical and extends axially along axis A. The inner surface 36 is also generally cylindrical and is coaxial with the outer surface 34.

Alternatively, the expandable support member 16 may include any known stent structure that is expandable and that defines the inner and outer surfaces 36 and 34, respectively. Although the apparatus 10 is illustrated as being cylindrical with a circular cross-sectional shape, the cross-sectional shape of the apparatus may alternatively be elliptical, polygonal, or cone-shaped.

Figures 4A, 4B:
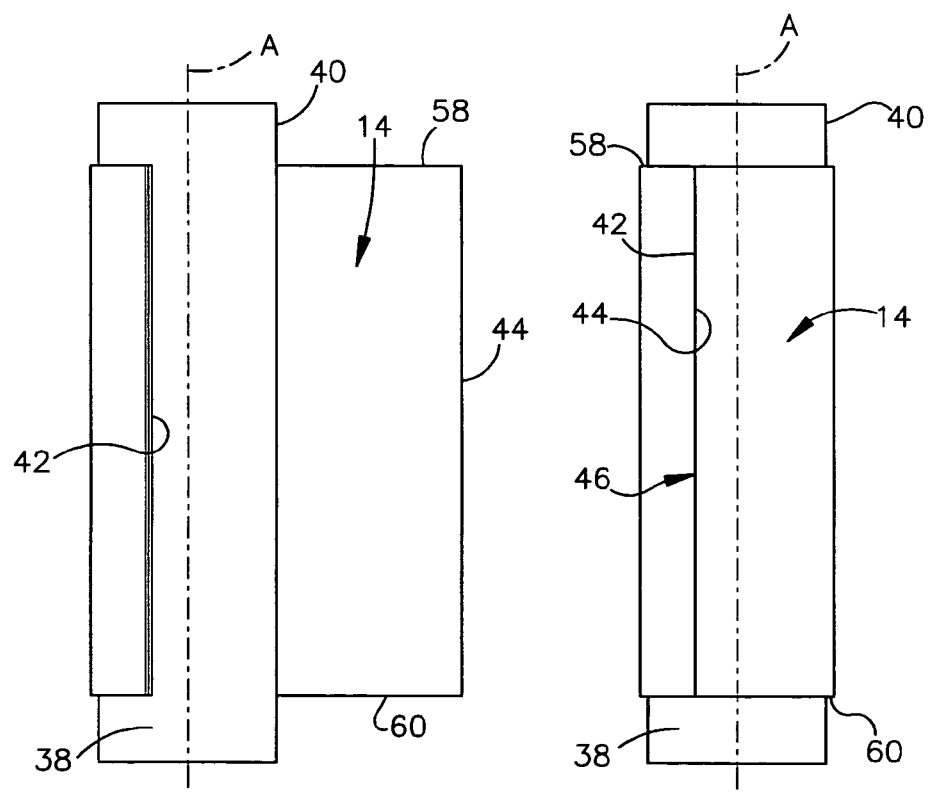
FIGS. 4a-4f illustrate a method for making the apparatus of FIG. 1.

FIGS. 4a-4f illustrate a method for forming the apparatus 10 of the present invention. The method begins at FIG. 4a with a dowel 38 and a sheet of biological tissue 14 that has been fixed and trimmed into a rectangular shape. The dowel 38 is formed from glass. The dowel 38 illustrated in FIG. 4a is cylindrical and has an outer surface 40 with a circular cross-sectional shape. Alternatively, the dowel 38 may be cone-shaped. A circumference of the outer surface 40 of the dowel 38 is equal to a width of the biological tissue 14. The width of the biological tissue 14 is defined as the distance between a first side surface 42 and a second side surface 44. FIG. 4a illustrates the biological tissue 14 being wrapped or rolled around the dowel 38.

FIG. 4b illustrates the biological tissue 14 completely wrapped around the dowel 38. When completely wrapped around the dowel 38, the first side surface 42 of the biological tissue 14 abuts, rather than overlaps, the second side surface 44 of the biological tissue 14. An axially extending seam 46 is defined at the location where the first side surface 42 and the second side surface 44 meet. The seam 46 extends along an axial length of the biological tissue 14. The axial length of the biological tissue 14 is defined as a distance between a first axial end 58 and a second axial end 60.

The first side surface 42 abuts the second side surface 44 such that the inner surface 48 (FIGS. 1-3) of the apparatus 10, which is defined by an inner surface 50 (FIGS. 1-3) of the inner lining 18 of the biological tissue 14, is smooth, continuous, and uninterrupted. Since the inner surface 48 of the apparatus 10 has no projections or irregularities, such as would be present if the biological tissue 14 were overlapped, thrombosis and platelet deposition at the seam 46 are resisted. An additional benefit of abutting the first and second side surfaces 42 and 44 of the biological tissue 14 together is that the smooth, continuous, and uninterrupted inner surface 48 of the apparatus 10 does not create turbulent flow through the apparatus.

Figure 4C:
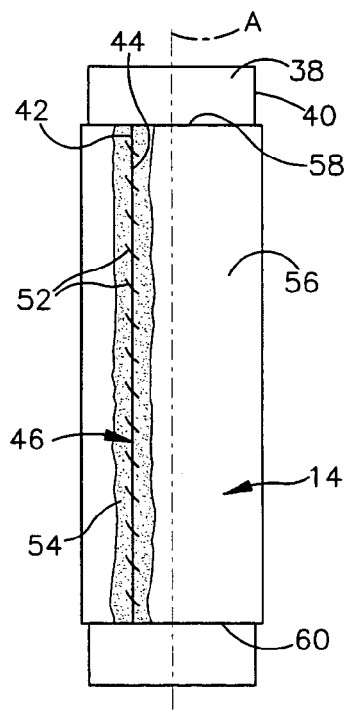

In FIG. 4c, the first side surface 42 of the biological tissue 14 is attached to the second side surface 44 of the biological tissue 14 using sutures 52. The sutures 52 extend radially inwardly through the biological tissue 14 and generally circumferentially between areas adjacent the first and second side surfaces 42 and 44. The biological tissue 14 remains on the dowel 38 while the sutures 52 are sewn in place. A layer of biological glue 54 may be placed over the seam 46 on an outer surface 56 of the biological tissue 14. The biological glue 54 helps to ensure that the inner surface 48 of the apparatus 10 remains smooth, continuous, and uninterrupted. The biological glue 54 also aids in completely sealing the seam 46 to prevent any leakage through the seam 46.

Figure 4D:
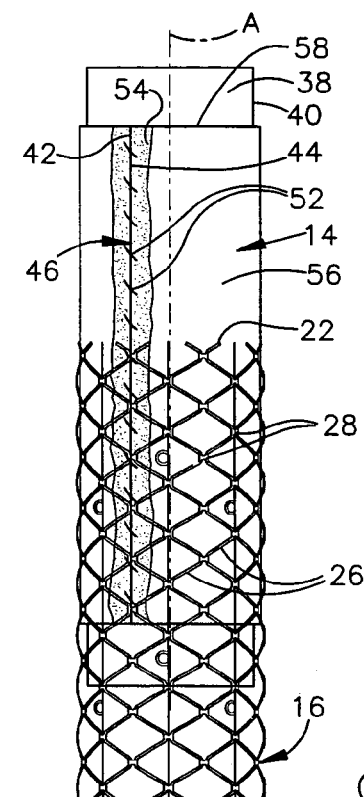

FIG. 4d illustrates the expandable support member 16 being placed over the biological tissue 14. The expandable support member 16 forms an outer support for the biological tissue 14. The expandable support member 16 forms the radially outermost component of the apparatus 10. The radially innermost component of the apparatus 10 is formed by the serous membrane lining 18 of the layer of biological tissue 14.

To place the expandable support member 16 over the biological tissue 14, the expandable support member 16 is expanded. Any known method for expanding the expandable support member 16 may be used, such as heating or balloon dilation of the expandable support member. The dowel 38 and the biological tissue 14 that is being held on the dowel 38 are inserted into the first end 22 of the expandable support member 16, as shown in FIG. 4d. The expandable support member 16 and the dowel 38 are moved relative to one another until an equivalent amount of biological tissue 14 extends axially outwardly of both the first and second ends 22 and 24 of the expandable support member 16.

The expandable support member 16 is then constricted until the inner surface 36 of the expandable support member 16 engages the outer surface 56 of the biological tissue 14 equally about the circumference of the outer surface 56 of the biological tissue 14. Next, the biological tissue 14 is attached to the expandable support member 16. Preferably, sutures (not shown) are used to attach the biological tissue 14 to the expandable support member 16. Each suture extends through the biological tissue 14 and a portion of the suture is threaded through one of the eyelets 29 of the expandable support member 16. The suture is then tied outside of the expandable support member 16 and around the respective eyelet 29. The suture holds the biological tissue 14 to the inner surface 36 of the expandable support member 16. The sutures are sufficiently small so that turbulent flow will not result from the interaction of blood flow with the sutures. Alternately, the outer surface 56 of the biological tissue 14 may be glued to the inner surface 36 of the expandable support member 16 using biological glue. When biological glue is used to attach the biological tissue 14 to the expandable support member 16, the support beams 26 and the support rods 27 must have an inner surface area large enough for adhesion of the biological tissue 14.

Figure 4E:
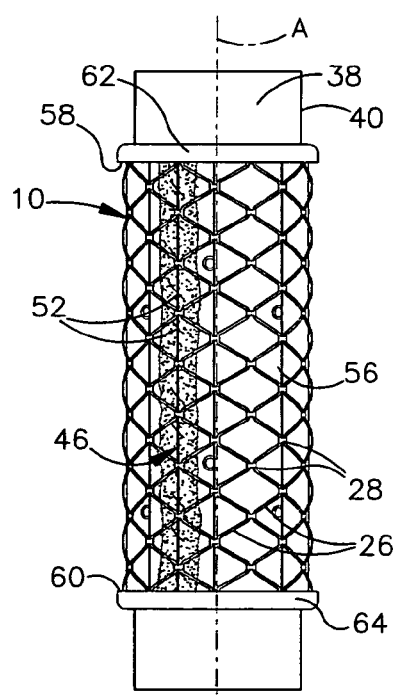

After the biological tissue 14 is attached to the expandable support member 16, the first and second axial ends 58 and 60 of the biological tissue 14 are folded over the first and second ends 22 and 24, respectively, of the expandable support member 16, as is shown in FIG. 4e. The first axial end 58 of the biological tissue 14 is stretched and folded over the first end 22 of the expandable support member 16 to form a first folded portion 62. The first folded portion 62 is then attached to the outer surface 34 of the expandable support member 16 using sutures (not shown). A second axial end 60 of the biological tissue 14 is stretched and folded over the second end 24 of the expandable support member 16 to form a second folded portion 64. The second folded portion 64 is also attached to the expandable support member 16 using sutures (not shown).

Figure 4F:
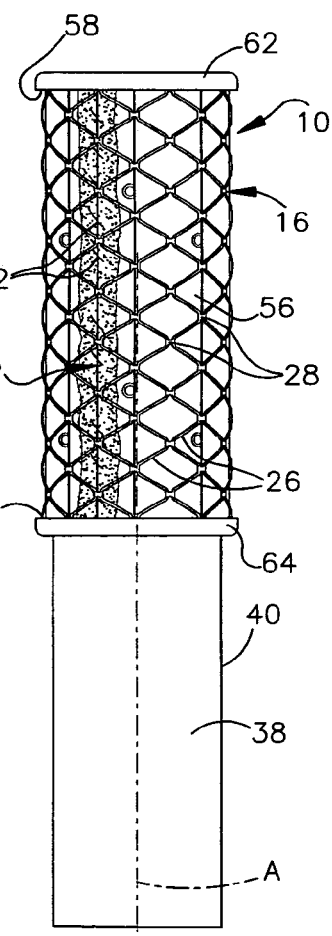

The apparatus 10, including the dowel 38, is stored in a sterile environment until it is time for implantation into a patient. Preferably, the apparatus 10 is submersed in a biological solution and is stored in a sterile, vacuum-packed container (not shown). Alternatively, the dowel 38 may be removed from the apparatus 10 prior to storing the apparatus. FIG. 4f illustrates the dowel 38 being removed from the apparatus 10. Preferably, the dowel 38 and the apparatus 10 are placed in biological or fixing solution to facilitate removal of the dowel 38 from inside the apparatus 10. The solution will sufficiently lubricate the dowel 38 and the biological tissue 14 so that the dowel may be removed from the apparatus 10 without tearing or weakening the biological tissue 14. As a result, the inner surface 48 of the apparatus 10 remains smooth, continuous, and uninterrupted. Alternatively, the apparatus 10 may be expanded and the dowel 38 removed from the expanded apparatus.

FIG. 5 illustrates the apparatus 10 of the present invention implanted in a blood vessel 12. The blood vessel 12 includes an outside surface 66 and an inside surface 68. The inside surface 68 of the blood vessel 12 forms a conduit for directing blood flow. The apparatus 10 is delivered and positioned in the blood vessel 12 using percutaneous or open surgical methods that are known in the art. Once the apparatus 10 is positioned in the desired location in the blood vessel 12, the expandable support member 16 is expanded, by a balloon (not shown) or through self-expansion as is known in the art. When the expandable support member 16 expands, a first end 70 of the apparatus 10 engages the blood vessel 12 such that an interference fit is created between the first folded portion 62 and the inside surface 68 of the blood vessel 12. Similarly, a second end 72 of the apparatus 10 engages the blood vessel 12 such that an interference fit is created between the second folded portion 64 and the inside surface 68 of the blood vessel 12. An interference fit is also created between the expandable support member 16 and the inner surface 68 of the blood vessel 12 along the axial length of the apparatus 10 that extends between the first and second ends 70 and 72. In addition to the interference fit between the expandable support member 16 and the blood vessel 12, sutures can also used to anchor the expandable support member 16 to the blood vessel 12.

When the apparatus 10 engages and adheres to the inside surface 68 of the blood vessel 12 in the above manner, the inner lining 18 of serous membrane forms the outermost surface at the first and second folded portions 62 and 64. The inner lining 18 bonds to the inside surface 68 of the blood vessel 12 in a normal tissue-healing fashion and prevents the in-growth of inflammatory tissue. As a result, the bond between the serous membrane of the inner lining 18 at the first and second folded portions 62 and 64 and the inside surface 68 of the blood vessel 12 prevents restenosis or occlusion. Additionally, the healing bond between the serous membrane of the inner lining 18 at the first and second folded portions 62 and 64 and the inside surface 68 of the blood vessel 12 forms more quickly than a bond between the fascia lining 20 and the inside surface 68 of the blood vessel 12.

When implanted in the blood vessel 12, the conduit formed by the inner surface 50 of the biological tissue 14 is confluent with the inside surface 68 of the blood vessel 12. The transition between the inside surface 68 of the blood vessel 12 and the inner surface 50 of the biological tissue 14 is smooth so that thrombosis and platelet deposition is resisted and that blood flow is not restricted when passing through the apparatus 10. The expandable support member 16 provides sufficient support against the internal pressure caused by the blood flow through the apparatus 10, and also resists radial collapse of the blood vessel.

Figure 6:
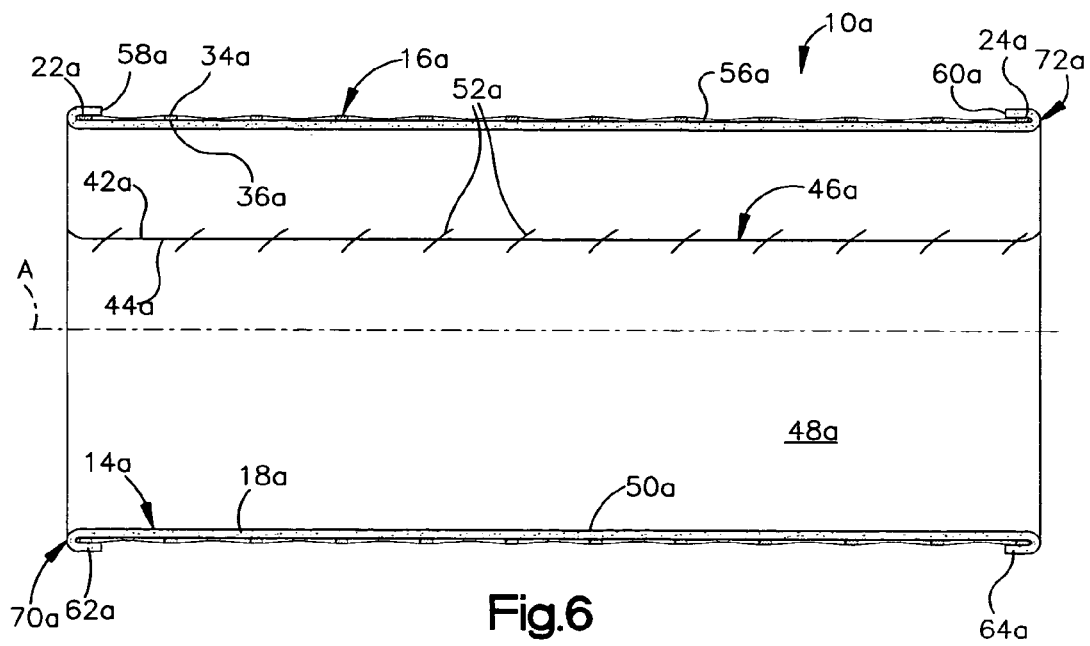
FIG. 6 is a longitudinal sectional view of a second embodiment of an apparatus constructed in accordance with the present invention.

FIG. 6 is a longitudinal sectional view of a second embodiment of an apparatus 10a constructed in accordance with the present invention. Structures of the embodiment shown in FIG. 6 that are similar to structures of FIGS. 1-3 have the same reference numbers with the suffix "a" added. The apparatus 10a is identical to apparatus 10 of FIGS. 1-3 with the exception that the layer of biological tissue 14a in the embodiment of FIG. 6 includes only a layer 18a of serous membrane.

The layer of biological tissue 14a is harvested to include only the layer 18a of serous membrane. The method for harvesting only a layer 18a of serous membrane is known in the art The assembly of apparatus 10a is identical to the assembly of apparatus 10 that is illustrated in FIGS. 4a-4f. When trimmed into the desired shape, the layer of biological tissue 14a includes first and second side surfaces 42a and 44a, respectively, and first and second axial ends 58a and 60a, respectively.

The assembled apparatus includes a seam 46a that is formed from abutting the first and second side surfaces 42a and 44a. The assembled apparatus 10a also includes first and second folded portions 62a and 64a. The first folded portion 62a is formed by folding the first axial end 58a of the layer of biological tissue 14a over the first end 22a of the expandable support member 16a. The second folded portion 64a is formed by folding the second axial end 60a of the layer of biological tissue 14a over the second end 24a of the expandable support member 16a.

The inner surface 48a of the assembled apparatus 10a is defined by the inner surface 50a of the layer 18a of serous membrane. The inner surface 148a of the apparatus 10a is smooth, continuous, and uninterrupted. The smooth, continuous, and uninterrupted inner surface 48a of the apparatus 10a resists thrombosis and platelet deposition.

Figure 7:
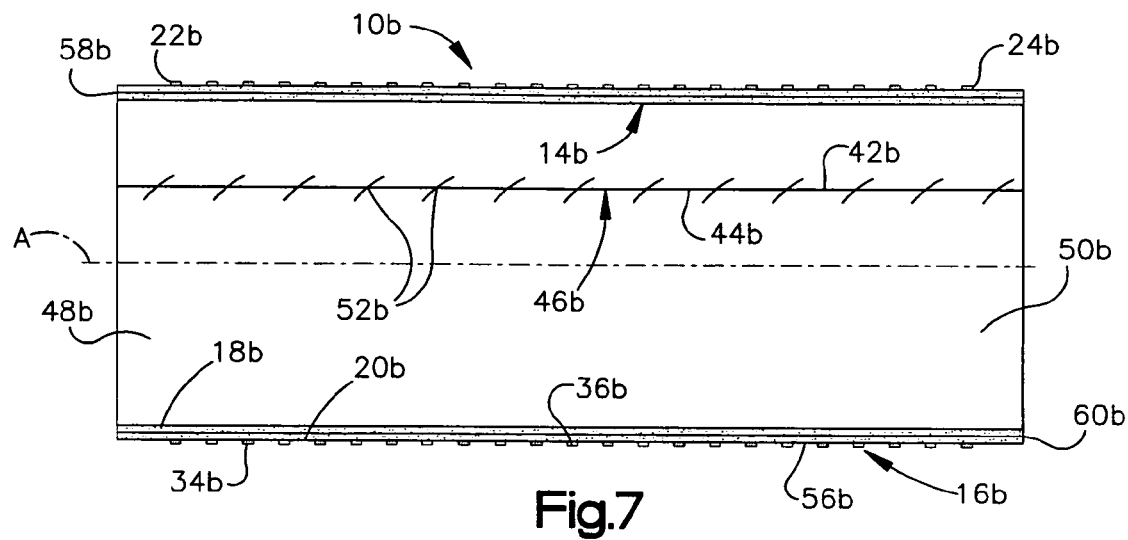
FIG. 7 is a longitudinal sectional view of a third embodiment of an apparatus constructed in accordance with the present invention.

FIG. 7 is a longitudinal sectional view of an apparatus 10b constructed in accordance with a third embodiment of the present invention. Structures of the embodiment shown in FIG. 7 that are similar to structures of FIGS. 1-3 have the same reference numbers with the suffix "b" added.

The apparatus 10b illustrated in FIG. 7 includes a layer of biological tissue 14b and an expandable support member 16b. The layer of biological tissue 14b includes a serous membrane lining 18b and associated fascia lining 20b. The expandable support member 16b has a structure similar to that illustrated in FIG. 1. The layer of biological tissue 14b forms the innermost component of the apparatus 10b.

The layer is biological tissue 14b is formed into a tubular portion by abutting first and second side surfaces 42b and 44b of the biological tissue 14b at a seam 46b. Preferably, the first and second side surfaces 42b and 44b are sutured together at the seam 46b and biological glue (not shown) is applied to an outer surface 56b of the biological tissue 14b.

The outer surface 56b of the layer of biological tissue 14b is attached to the inner surface 36b of the expandable support member 16b. The expandable support member 16b is placed over the biological tissue 14b such that equal amounts of biological tissue 14b extend from the first and second ends 22b and 24b of the expandable support member 16b. Instead of folding the first and second axial ends 58b and 60b of the biological tissue 14b over the expandable support member 16b as discussed above with regard to the embodiment of FIGS. 1-3, the first and second axial ends 58b and 60b of the biological tissue 14b extend axially beyond the first and second ends 22b and 24b of the expandable support member 16b. Thus, in assembling the apparatus 10b, the step illustrated in FIG. 4e is omitted.

When implanted into a blood vessel of a patient, the first and second axial ends 58b and 60b of the tissue 14b engage and are adhered to the inside surface of the blood vessel by the expansion of the expandable support member 16. The extension of the first and second axial ends 58b and 60b of the biological tissue 14b axially beyond the first and second ends 22b and 24b of the expandable support member 16b allows the first and second axial ends of the biological tissue to be sutured directly to the inside surface of the blood vessel.

Figure 8:
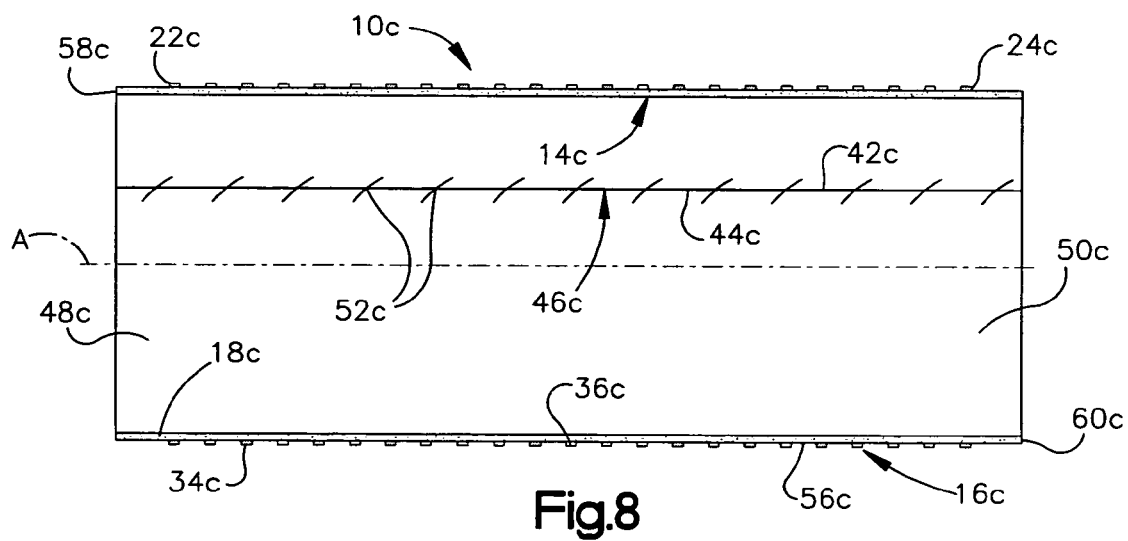
FIG. 8 is a longitudinal sectional view of a fourth embodiment of an apparatus constructed in accordance with the present invention.

FIG. 8 is a longitudinal sectional view of a fourth embodiment of an apparatus 10c constructed in accordance with the present invention. Structures of the embodiment shown in FIG. 8 that are similar to structures of FIG. 7 have the same reference numbers with the suffix "c" replacing the suffix "b". The apparatus 10c is identical to apparatus 10b of FIG. 7 with the exception that the layer of biological tissue 14c in the embodiment of FIG. 8 includes only a layer 18c of serous membrane.

The assembly of apparatus 10c is identical to the assembly of apparatus 10b. When trimmed into the desired shape, the layer of biological tissue 14c includes first and second side surfaces 42c and 44c, respectively, and first and second axial ends 58c and 60c, respectively.

The assembled apparatus includes a seam 46c that is formed from abutting the first and second side surfaces 42c and 44c. The inner surface 48c of the assembled apparatus 10c is defined by the inner surface 50c of the layer 18c of serous membrane. The inner surface 48c of the apparatus 10c is smooth, continuous, and uninterrupted. The smooth, continuous, and uninterrupted inner surface 48c of the apparatus 10c resists thrombosis and platelet deposition.

Figure 9:
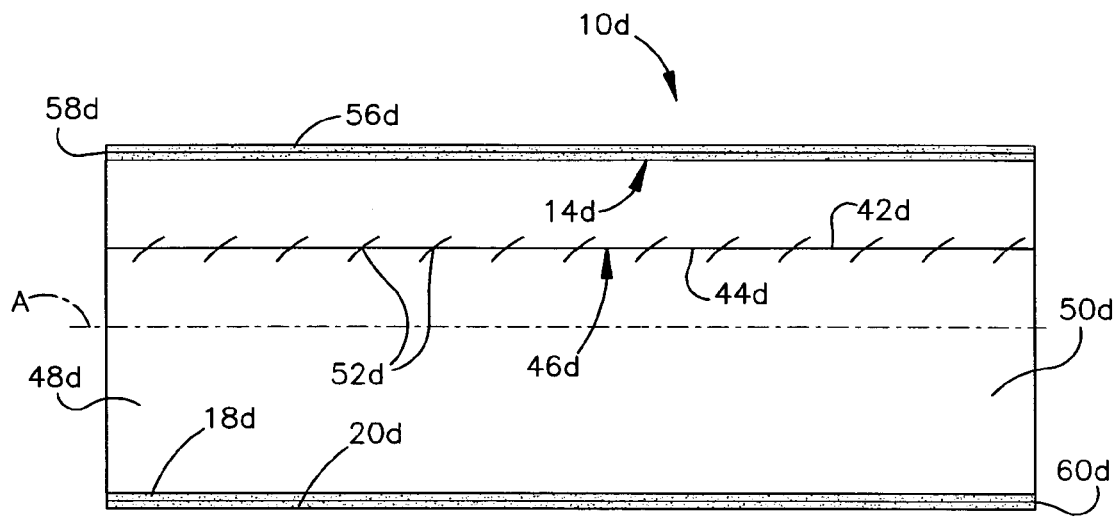
FIG. 9 is a longitudinal sectional view of a fifth embodiment of an apparatus constructed in accordance with the present invention.

FIG. 9 illustrates a longitudinal sectional view of a fifth embodiment of an apparatus 10d constructed in accordance with the present invention. Structures of the embodiment shown in FIG. 9 that are similar to structures of FIG. 7 have the same reference numbers with the suffix "d" replacing the suffix "b".

The apparatus 10d of FIG. 9 is also a cardiovascular graft. The apparatus 10d includes a layer of biological tissue 14d that includes an inner lining 18d of serous membrane and an outer lining 20d of fascia associated with the serous membrane. The layer of biological tissue 14d is rectangular and includes first and second side surfaces 42d and 44d, respectively, and first and second axial ends 58d and 60d, respectively. The inner lining 18d of serous membrane includes an inner surface 50d. The outer lining 20d of fascia includes an outer surface 56d.

The apparatus 10d illustrated in FIG. 9 is cylindrical and is formed by the layer of biological tissue 14d. The first and second side surfaces 42d and 44d of the layer of biological tissue 14d are abutted and secured together to define a seam 46d. Sutures 52d attach the first and second side surfaces 42d and 44d at the seam 46d. A layer of biological glue (not shown) is applied to the outer surface 56d of the outer lining 20d over the seam 46d. The biological glue aids in completely sealing the seam 46d to prevent any leakage through the seam.

To form the apparatus 10d, the steps illustrated in FIGS. 4a to 4c and discussed in detail with regards to apparatus 10 of FIGS. 1-3 are followed. After the step shown in FIG. 4c, the apparatus 10d is stored in a sterile environment until it is time for implantation into a patient. Prior to implantation into the patient, the dowel is removed from the apparatus.

The outer surface 56d of the outer lining 20d forms the outermost component of the apparatus 10d. The inner surface 50d of the inner lining 18d of serous membrane forms the innermost component of the apparatus 10d. The inner surface 50d of the inner lining 18d is smooth, continuous, and uninterrupted. As a result, the inner surface 48d of the apparatus 10d is smooth, continuous, and uninterrupted and resists thrombosis and platelet deposition.

When surgically implanted in a patient, the apparatus 10d is attached using sutures. For example, when used within a blood vessel, the apparatus 10d is sutured to the inside surface of the blood vessel. As a result, the continuous and uninterrupted inner surface 50d of the inner lining 18d is confluent with the inside surface of the blood vessel.

Since the apparatus 10d includes no support structures, the apparatus adapts or conforms to the shape of the blood vessel into which it is attached. Thus, if the inside surface of the blood vessel has an elliptical cross-sectional shape, the apparatus 10d, when attached to the inside surface of the blood vessel, has an elliptical cross-sectional shape.

Figure 10:
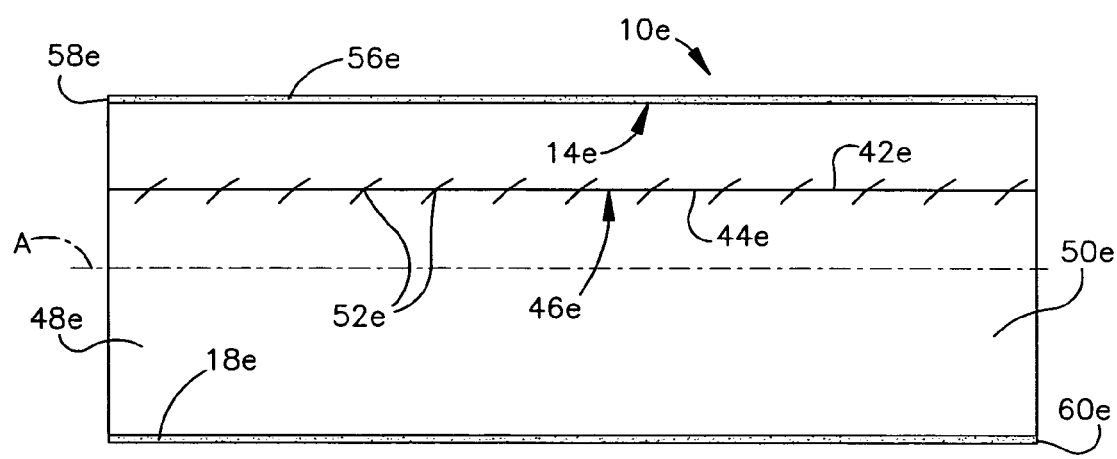
FIG. 10 is a longitudinal sectional view of a sixth embodiment of an apparatus constructed in accordance with the present invention.

FIG. 10 is a longitudinal sectional view of a sixth embodiment of an apparatus 10e constructed in accordance with the present invention. Structures of the embodiment shown in FIG. 10 that are similar to structures of FIG. 9 have the same reference numbers with the suffix "e" replacing the suffix "d". The apparatus 10e is identical to apparatus 10d of FIG. 9 with the exception that the layer of biological tissue 14e in the embodiment of FIG. 10 includes only a layer 18e of serous membrane.

The assembly of apparatus 10e is identical to the assembly of apparatus 10e. When trimmed into the desired shape, the layer of biological tissue 14e includes first and second side surfaces 42e and 44e, respectively, and first and second axial ends 58e and 60e, respectively.

The assembled apparatus includes a seam 46e that is formed from abutting the first and second side surfaces 42e and 44e. The inner surface 48e of the assembled apparatus 10e is defined by the inner surface 50e of the layer 18e of serous membrane. The inner surface 48e of the apparatus 10e is smooth, continuous, and uninterrupted. The smooth, continuous, and uninterrupted inner surface 48e of the apparatus 10e resists thrombosis and platelet deposition.

Figure 11:
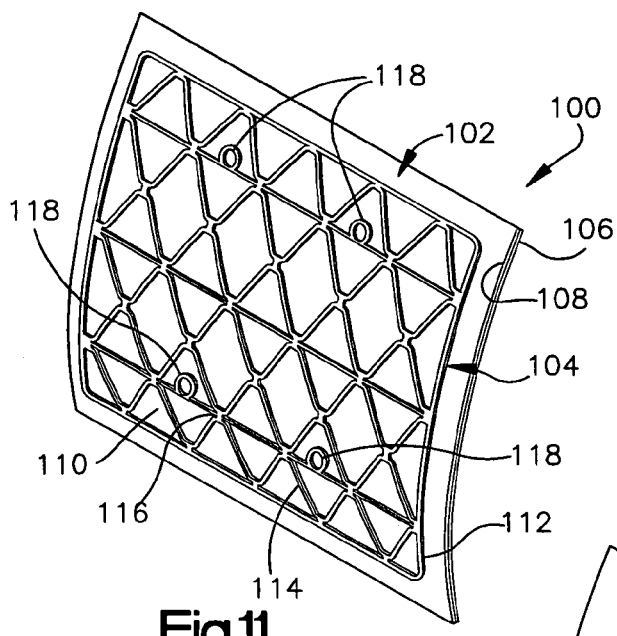
FIG. 11 is a perspective view of a seventh embodiment of an apparatus constructed in accordance with the present invention.

FIG. 11 illustrates a perspective view of a seventh embodiment of an apparatus 100 constructed in accordance with the present invention. The apparatus 100 in FIG. 11 is a patch for repairing a portion of a blood vessel or other membrane within the cardiovascular system of the human body.

The patch 100 includes a layer of biological tissue 102 and an outer support member 104. The layer of biological tissue 102 includes a serous membrane lining 106 and associated fascia lining 108. The serous membrane lining 106 forms an inner surface (not shown) of the biological tissue 102 and the associated fascia 108 forms an outer surface 110 of the biological tissue 102. The layer of biological tissue 102 is illustrated as being rectangular but may be of any desired shape.

The outer support member 104 has the same shape as the biological tissue 102 but is slightly smaller is size. The outer support member 104 may have a curved profile, as is illustrated in FIG. 11, for fitting to a curved surface such as the inside or outside surfaces of a blood vessel.

The outer support member 104 in FIG. 11 is rectangular and includes an outer frame 112 and inner support beams 114. The outer frame 112 defines the shape of the outer support member 104 and provides support near the periphery of the biological tissue 102. The inner support beams 114 of the outer support member 104 provide support for an interior portion of the biological tissue 102. Eyelets 118 are provided through which sutures (not shown) may be threaded when attaching the biological tissue 102 to the outer support member 104.

The outer surface 110 of the biological tissue 102 is attached to the outer support member 104. Preferably, the biological tissue 102 is sutured to the outer support member 104. The peripheral portion of the biological tissue 102 extends outwardly from the outer support member 104. Alternatively, the peripheral portion of the biological tissue 102 may be folded over the outer frame 112 of the outer support member 104.

When implanted in a blood vessel, an outer surface 116 of the outer support member 104 of the patch 100 is placed over an aneurysm or a weakened portion of the blood vessel. The size of the outer support member 104 is preferably larger than the aneurysm or weakened portion of the blood vessel such that the outer frame 112 of the outer support member 104 contacts healthy portions of the inside surface of the blood vessel. The outer periphery of the biological tissue 102 is then attached to the inside surface of the blood vessel, preferably by suturing. The patch 100 may alternatively be placed over the outside surface of the blood vessel or be used on another membrane of the cardiovascular system.

Figure 12:
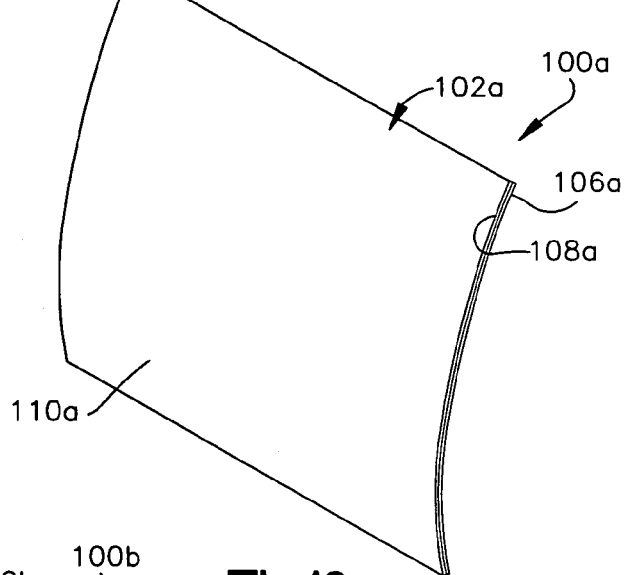
FIG. 12 is a perspective view of an eighth embodiment of an apparatus constructed in accordance with the present invention.

FIG. 12 is a view of an eighth embodiment of an apparatus 100a constructed in accordance with the present invention. Structures of the embodiment shown in FIG. 12 that are similar to structures of FIG. 11 have the same reference numbers with the suffix "a" added.

The apparatus 100a of FIG. 12 is also a patch for repairing a portion of a blood vessel or other membrane within the cardiovascular system of the human body. The patch 100a includes a layer of biological tissue 102a. The patch 100a of FIG. 12 does not include a support structure such as the outer support structure 104 illustrated in FIG. 11.

The layer of biological tissue 102a includes a serous membrane lining 106a and associated fascia lining 108a. The serous membrane lining 106a forms an inner surface (not shown) of the biological tissue 102a and the associated fascia 108a forms an outer surface 110a of the biological tissue 102a. The inner surface of the biological tissue 102a is smooth, continuous, and uninterrupted. The layer of biological tissue 102a is illustrated as being rectangular but may be of any desired shape.

When implanted in a blood vessel, an outer surface 110a of the associated fascia 108a of the layer of biological tissue 102a is placed over an aneurysm or a weakened portion of the blood vessel. The biological tissue 102a is then attached to the inside surface of the blood vessel, preferably by suturing. Since the patch 100a does not include structural support, the patch 100a easily adapts to the shape of the blood vessel or membrane to which it is attached to ensure a sufficient area of contact between patch 100a and the blood vessel or membrane. The patch 100a may alternatively be placed over the outside surface of the blood vessel or be used on another membrane of the cardiovascular system.

Figure 13:
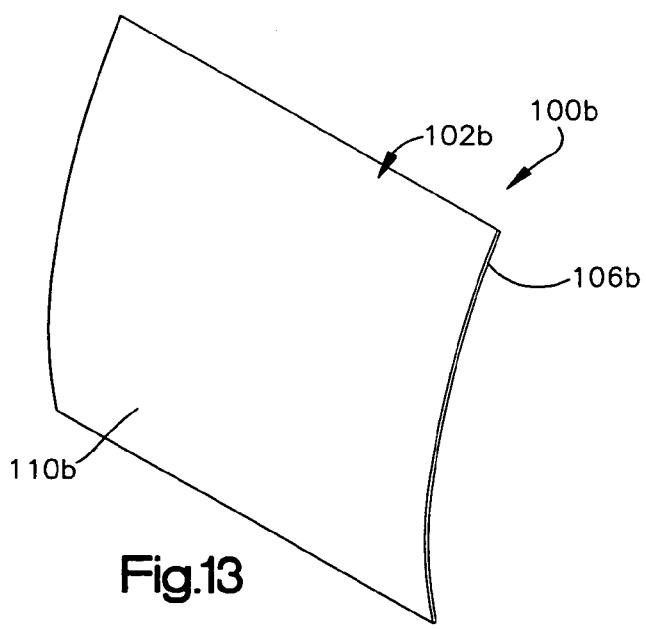
FIG. 13 is a perspective view of a ninth embodiment of an apparatus constructed in accordance with the present invention.

FIG. 13 is a perspective view of a ninth embodiment of an apparatus 100b constructed in accordance with the present invention. Structures of the embodiment shown in FIG. 13 that are similar to structures of FIG. 12 have the same reference numbers with the suffix "b" replacing the suffix "a". The apparatus 100b is identical to apparatus 100a of FIG. 12 with the exception that the layer of biological tissue 102b in the embodiment of FIG. 13 includes only a layer 106b of serous membrane.

The outer surface 110b of the biological tissue 102b is formed by an outer surface of the layer 106b of serous membrane. The inner surface (not shown) of the biological tissue is formed by an inner surface of the layer 106b of serous membrane and is smooth, continuous and uninterrupted.

Figure 14:
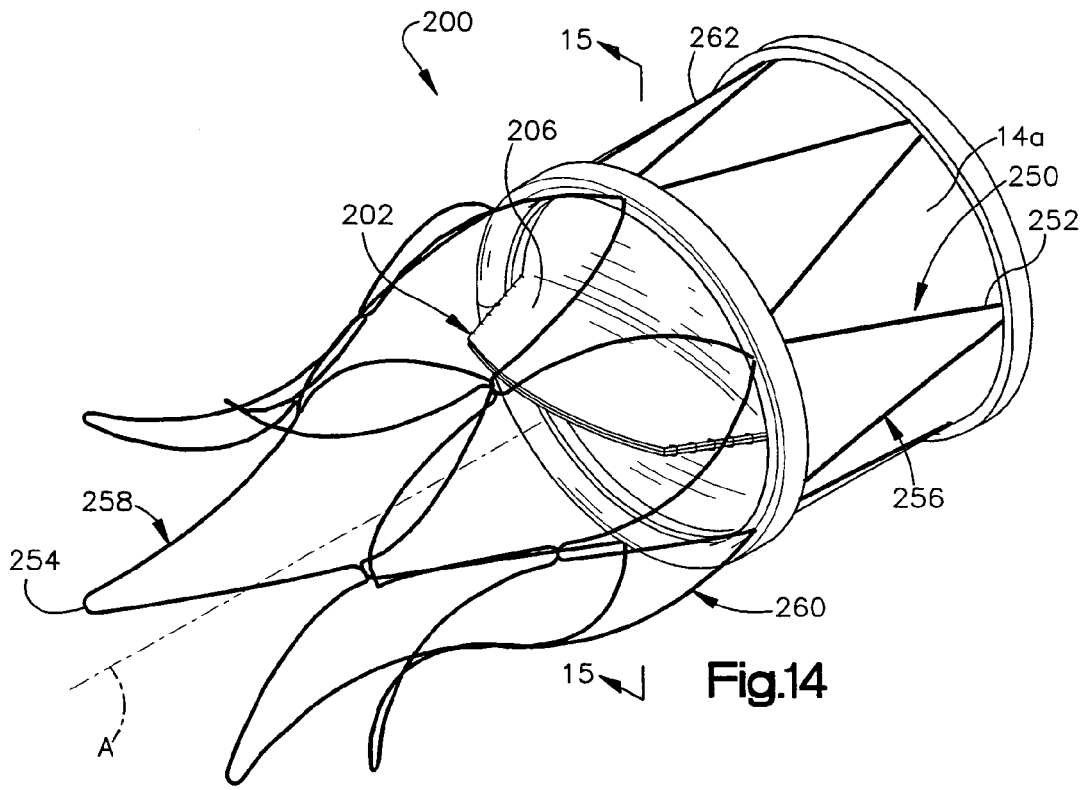
FIG. 14 is a perspective view of a tenth embodiment of an apparatus constructed in accordance with the present invention.
Figure 15:
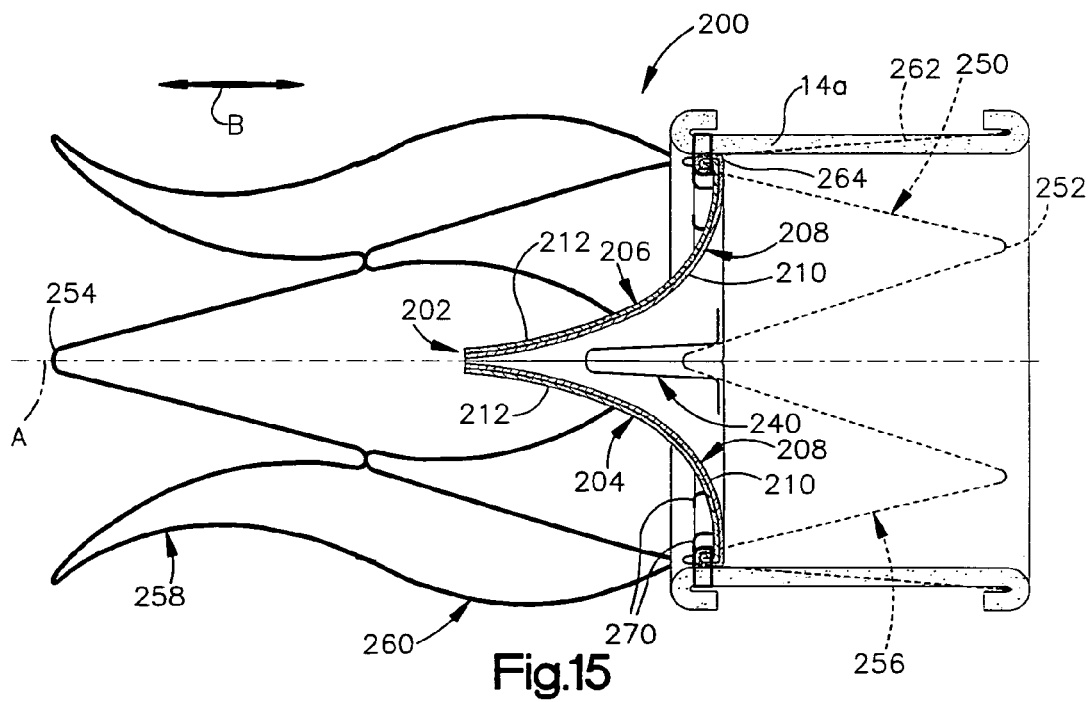
FIG. 15 is a section view taken along line 15-15 in FIG. 14.

FIGS. 14 and 15 illustrate a tenth embodiment of an apparatus 200 constructed in accordance with the present invention. Structures of the tenth embodiment shown in FIGS. 14 and 15 that are the same as structures described in the previous embodiments have the same reference numbers.

According to the tenth embodiment, the apparatus 200 comprises a prosthetic valve 202 for placement in a body passage, such as within a blood vessel or between chambers of the heart. The valve 202 includes two valve leaflets 204 (FIG. 15) and 206, an expandable support member (or stent) 250, and the layer of biological tissue 14*a* (described above with regards to the embodiment of FIG. 6). It should be understood by those skilled in the art that the valve 202 could have more than two leaflets depending on the needs of the specific implantation.

The valve leaflets 204 and 206 are made from a layer of biological material 208. The layer of biological material 208 may be either harvested peritoneal fascia tissue, harvested pleural tissue, or harvested pericardial tissue. The layer of biological material 208 may be autogenous, xenogenous, or cadaveric. In the tenth embodiment, the layer of biological material includes an inner lining 210 (FIG. 15) and an outer lining 212. The inner lining 210 is a serous membrane and the outer lining 212 is fascia associated with the serous membrane.

The layer of biological material 208 may be harvested in sheets of appropriate size using conventional techniques. The layer of biological material 208 is then fixed or preserved with alcohol, glutaraldehyde, and/or another biological solution. After being fixed, the layer of biological material 208 is trimmed or cut into the desired shape and size. It is noted that the layer of biological material 208 may shrink slightly when fixed. Thus, the layer of biological material 208 should be fixed prior to being trimmed to the desired shape and size. In accordance with the tenth embodiment, the layer of biological material 208 is trimmed into the two semi-elliptical pieces shown in FIGS. 17A and 17B. After being trimmed, the layer of biological material 208 may be bathed in the biological solution.

Each of the two valve leaflets 204 and 206 has a periphery defined by a semi-circular edge portion 220 (FIG. 17A), a free edge portion 222, and an oppositely disposed pair of lateral side portions 224 and 226. The lateral side portions 224 and 226 extend on either side of the free edge portions 222 to the circular edge portions 226. The lateral side portions 224 and 226 of each of the two valve leaflets 204 and 206 adjoin each other and are attached to each other by sutures 228 (FIG. 16) to form two commissural sides 230 and 232 of the valve 202 that are separated by the free edge portions 222. The free edge portions 222 remain unattached and define an opening 234 (FIG. 16) through which blood flows through the valve 202. The free edge portions 222 are coaptable to provide for the unidirectional flow of blood.

In accordance with one aspect of the invention, the valve 202 further includes a pair of strut members 240 (FIG. 17A) for supporting the valve leaflets 204 and 206 in their proper shape and position, and for preventing prolapse of the valve leaflets during diastole. The strut members 240 are located at each of the two commissural sides 230 and 232 formed by the junctions of the adjoining lateral side portions 224 and 226 of the two valve leaflets 204 and 206. The strut members 240 may be made from any suitable medical grade metal or plastic, including shape memory materials such as Nitinol.

Each of the two strut members 240 has an upside-down U-shape formed by a pair of leg portions 242 that are connected by a bridge portion 244. A wing portion 246 extends outward from each of the leg portions 242 to provide a structural base for the strut members 240. One of the leg portions 242 of each strut member 240 is sewn to one of the lateral side portions 224 of each of the valve leaflets 204 and 206, and the other leg portion of each strut member is sewn to the other lateral side portion 226 of each of the valve leaflets. The bridge portion 244 of each of the strut members 240 extends across the junction of the adjoining lateral side portions 224 and 226 of the valve leaflets 204 and 206 adjacent the free edge portions 222. The wing portions 246 of each strut member 240 are sewn into the respective semi-circular edge portions 220 of each valve leaflet 204 and 206. As may be seen in the alternate configuration of FIG. 17B, the wing portions 246 may be lengthened and curved to provide additional structural support for the strut members 240.

The support member (or stent) 250 has a generally tubular shape that extends axially between oppositely disposed first and second ends 252 (FIG. 15) and 254. The support member 250 comprises an interconnected plurality of V-shaped braces, however it should be understood that other stent configurations could be used for the support member. The support member 250 is made from an expandable metal, such as Nitinol, but may alternatively be made from any suitable expandable material or shape memory material, including shape memory plastics.

The support member 250 includes oppositely disposed proximal and distal end sections 256 and 258. A center section 260 of the support member 250 extends between the end sections 256 and 258. For purposes of this disclosure, the term "proximal" means on the inflow or upstream side of the apparatus 200, and the term "distal" means on the outflow or downstream side of the apparatus.

The proximal end section 256 of the support member 250 has a generally planar shape in the axial direction, which is indicated by arrow B. The center section 260 of the support member 250 has a convex shape in the axial direction B. The distal end section 258 of the support member 250 has a concave shape in the axial direction B.

The tubular shape of the support member 250 defines coaxially extending cylindrical outer and inner surfaces 262 and 264. Although the outer and inner surfaces 262 and 264 are illustrated as having a circular cross-section, it is contemplated that they may have other cross-sectional shapes to match the shape of a particular valve annulus. The support member 250 includes a plurality of radiopaque markers (not shown) attached to the outer surface 262 for guiding placement of the apparatus 200 in a percutaneous delivery as is known in the art. The outer surface 262 of the support member 250 may also include a plurality of hooks or barbs (not shown) for helping to secure the apparatus 200 to a cardiac wall.

The layer of biological tissue 14*a* is attached to the inner surface 264 of the support member 250. In accordance with the tenth embodiment, the layer of biological tissue 14*a* comprises a serous membrane of either peritoneal fascia tissue, pleural tissue, or pericardial tissue that extends along a portion of the length of the support member 250. The layer of biological tissue 14*a* includes the radially inwardly facing surface 48 that defines a conduit for directing blood flow. It should be understood that the layer of biological tissue could also comprise an inner lining 18 of a serous membrane and an outer lining 20 of associated fascia as described in the first embodiment of FIGS. 1-5. In accordance with the tenth embodiment of the present invention, the layer of biological tissue 14*a* is attached to the inside surface 264 in only the proximal end section 256 of the support member 250, and thus the center section 260 and the distal end section 258 of the support member are bare.

The valve leaflets 204 and 206 are attached inside the layer of biological tissue 14a near the junction of the proximal end section 256 of the support member 250 and the center section 260. The leaflets 204 and 206 extend across the conduit defined by the layer of biological 14a and are structurally supported by the support member 250. The valve leaflets 204 and 206 are secured to the support member 250 and the layer of biological tissue 14a using sutures 270. The semi-circular edge portions 220 of the valve leaflets 204 and 206 may be rolled up, as shown in FIG. 15, to ensure sufficient material is present for suturing to the support member 250 and to the layer of biological tissue 14a that lines the support member.

Figure 18:
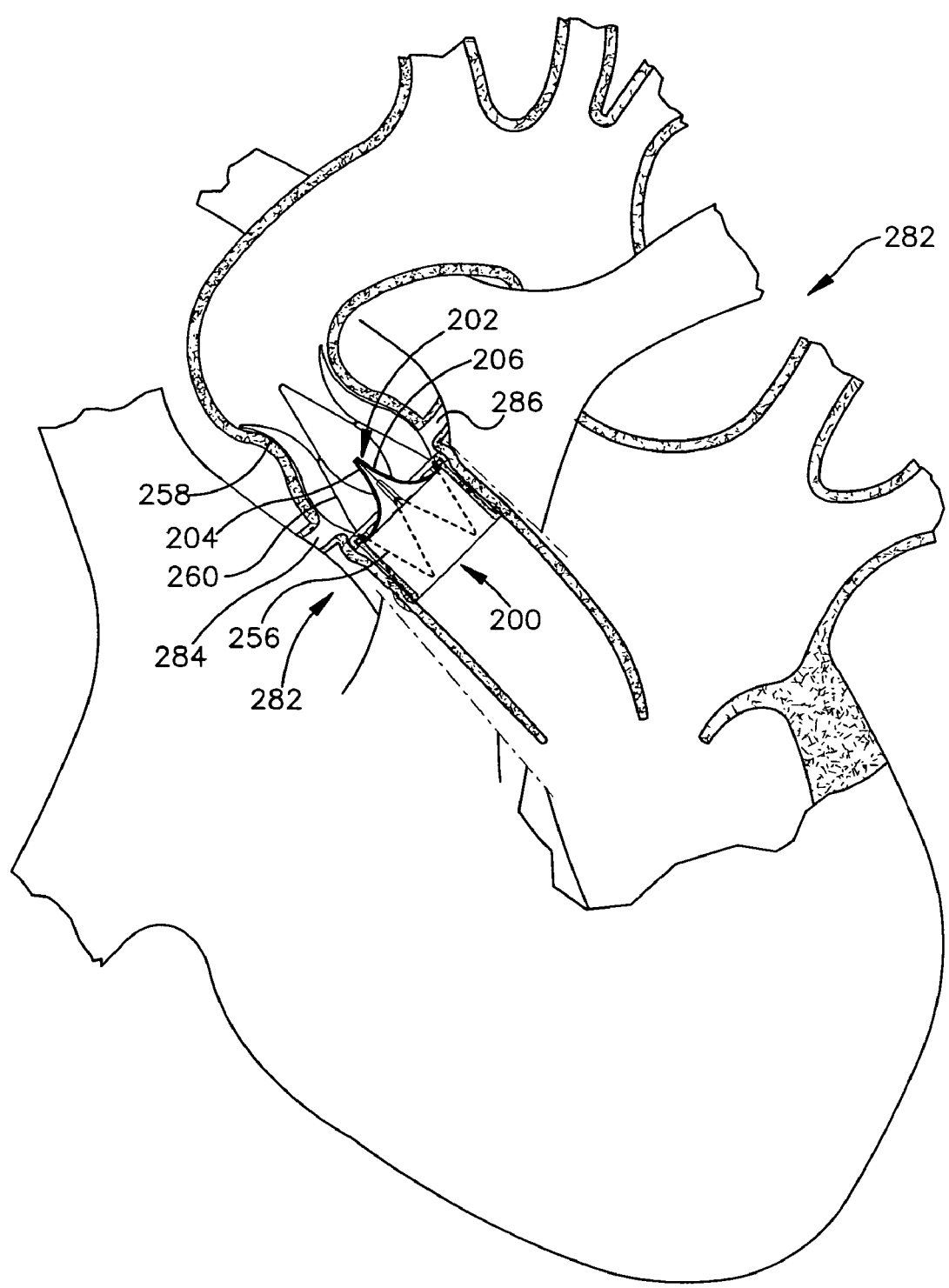
FIG. 18 is a schematic sectional view illustrating the apparatus of FIG. 14 implanted in the aortic valve position of a heart.

FIG. 18 schematically illustrates the apparatus 200 of the present invention implanted in the aortic valve position 280 of a heart 282. The apparatus 200 is delivered and positioned in the aortic valve position 280 using a minimally invasive percutaneous approach under fluoroscopic and/or echocardiographic guidance. It is contemplated that the apparatus 200 can be delivered with a percutaneous delivery system of 10 to 40 French using the Seldinger technique or other suitable minimally invasive percutaneous technique. The apparatus 200 may also be delivered and positioned using open surgical methods known in the art. The apparatus 200 may be positioned so as to expand and cover over the native valve leaflets or, if an open surgical procedure is being utilized, the native leaflets may be excised prior to positioning the apparatus 200 in the aortic valve location 280.

The apparatus 200 is positioned so that the proximal end section 256 lies in the annulus of the native aortic valve and the center section 260 lies radially inward of the coronary ostiums 284 and 286. The proximal end section 256, the distal end section 258, and the center section 260 of the support member 250 are then expanded by a combination mechanism that includes an inflatable balloon and self-expansion as discussed below with regard to FIGS. 18A-18C. A unique feature of the present invention is that the apparatus 200 may be self-expanded, balloon-expanded, or the aforementioned combination of balloon and self-expansion.

FIG. 18A illustrates the apparatus 200 in a radially compressed condition prior to implantation. The apparatus 200 has been loaded onto a catheter (or guidewire) 272 that includes an inflatable balloon 274. The proximal end section 256 encircles and is compressed about the balloon 274. The distal end and center sections 258 and 260 are compressed and are held in that condition by a constraining wire 276. It should be understood that the constraining wire 276 could have a number of different configurations known in the art. It should also be understood that other known devices (not shown) such as a sheath and a dilator (or nose cone) may be used in conjunction with the catheter 272 and the balloon 274 in order to deliver the apparatus 200 to the desired location. As shown sequentially in FIGS. 18B and 18C, to deploy the apparatus 200 in a desired location, the balloon is inflated first to expand the proximal end section 256, followed by releasing the constraining wire 276 which then allows the distal end and center sections 258 and 260 to self-expand.

Referring again to FIG. 18, the proximal end section 256 of the support member 250 expands into annular engagement with the valve annulus and creates an interference fit against the inside surface of the annulus. At the same time, the center section 260 of the support member 250 expands into engagement with the cardiac wall that lies downstream (or distal) of the valve annulus. As shown in FIG. 18, the convex shape of the center section 260 conforms to the shape of the cardiac wall in that location and allows for full annular engagement. Because the center section 260 of the support member 250 is bare (i.e. not lined with the biological material 14a), blood flow to the coronary ostiums 284 and 286 in not blocked by any part of the apparatus 200. The distal end section 258 of the support member 250 expands into engagement with the cardiac/vessel wall that lies downstream (or distal) of the coronary ostiums 284 and 286. As shown in FIG. 18, the concave shape of the distal end section 258 conforms to the shape of the cardiac/vessel wall in that location and allows for full annular engagement.

In addition to the interference fit between the expandable support member 250 and the aortic valve annulus, barbs (not shown) on the outer surface 262 of the support member help further secure the apparatus 200 in the annulus. If the apparatus 200 is being implanted in an open procedure, sutures can also be used to anchor the expandable support member 250 to the valve annulus.

When the apparatus 200 is implanted in the aortic valve location 280, the smooth inner surface 48 of the layer of the biological tissue 14a resists thrombosis and platelet deposition. The support member 250 provides sufficient support for the valve leaflets 204 and 206 against internal pressure caused by the blood flow through the apparatus 200. Further, by utilizing the shape memory properties of the material of the support member 250, the apparatus 200 can be used to remodel the profile of a dilatated native valve to a predetermined memorized shape and size.

The implanted apparatus 200 provides a fully functioning prosthetic valve 202 that, by virtue of the strut members 240, prevents prolapse of the leaflets 204 and 206. The biological materials used to make the leaflets 204 and 206 and to line the support member 250, provide the valve 202 with a high resistance to thrombosis. Thus, post-surgical systemic anti-coagulation medication is avoided. Further, the harvested peritoneal fascia, pleural, or pericardial tissue used for the leaflets 204 and 206 is significantly stronger than most tissue valves, such as bovine tissue valves, and thus provides the valve 202 with the long term durability. Finally, the apparatus 200 provides a prosthetic valve 202 that can be delivered percutaneously to the heart, thereby avoiding the trauma and associated risks of a surgical procedure in which the thoracic cavity is opened and a heart-lung machine is used.

Figure 19:
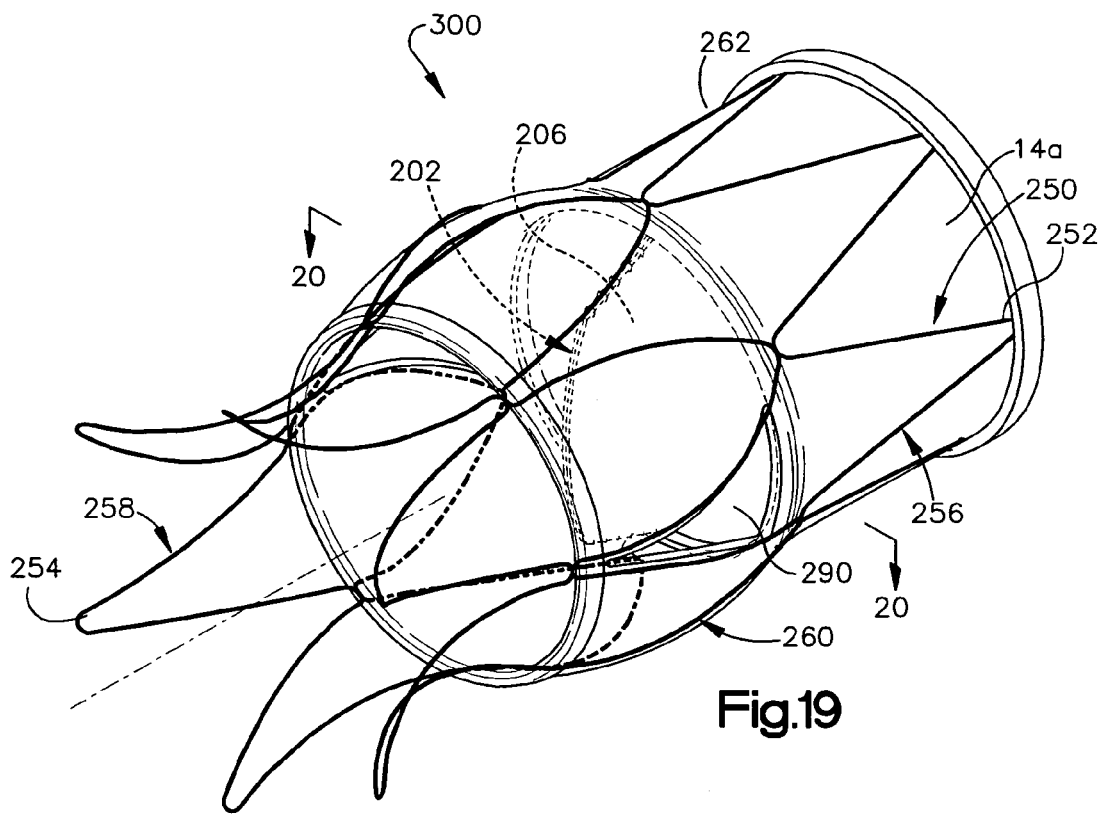
FIG. 19 is a perspective view of an eleventh embodiment of an apparatus constructed in accordance with the present invention.
Figure 20:
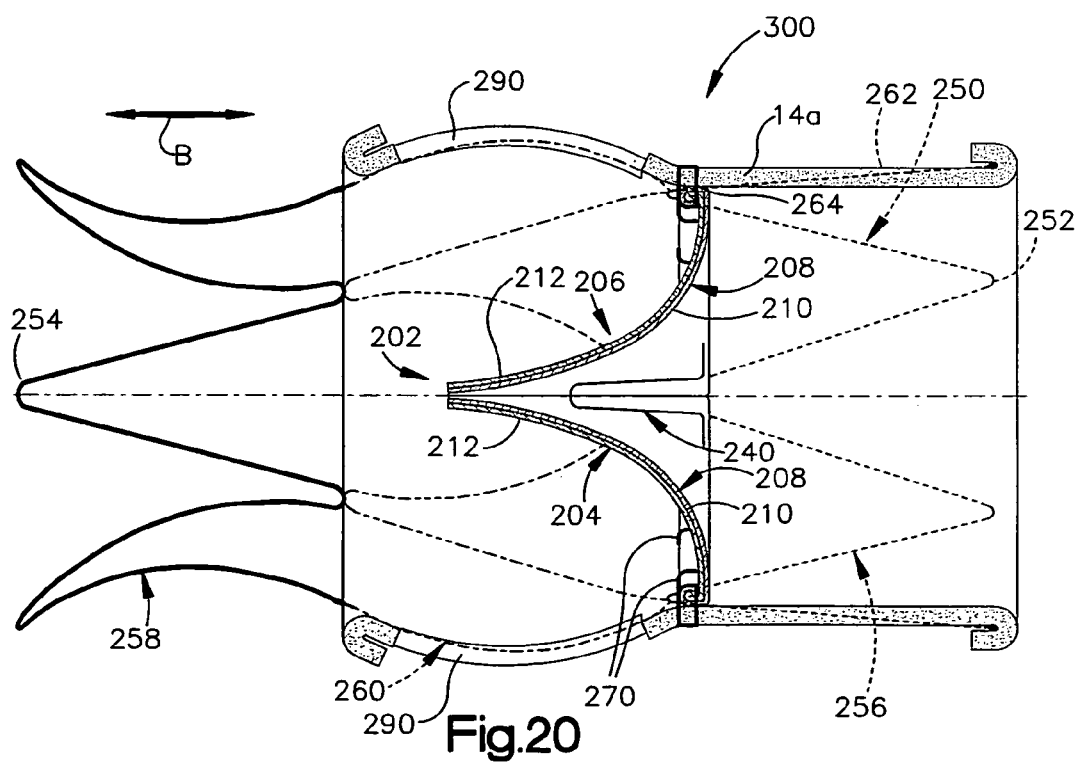
FIG. 20 is a section view taken along line 20-20 in FIG. 19.

FIGS. 19 and 20 illustrate an apparatus 300 constructed in accordance with an eleventh embodiment of the present invention. In the eleventh embodiment of FIGS. 19 and 20, structures of the eleventh embodiment that are the same as structures described in the tenth embodiment of FIGS. 14-18 have the same reference numbers.

The difference between the apparatus 300 and the previously described apparatus 200 is that the layer of biological material 14a extends through the center section 260 of the support member 250. The layer of biological material 14a thus extends along, and is attached to, the inner surface 264 of the support member 250 in both the proximal end section 256 and the center section 260. During manufacture of the apparatus 300, a pair of openings 290 are formed in the layer of biological material 14a in the center section 260 of the support member 250. FIG. 19 shows the openings 290 having a triangular shape to match the configuration of the support member 250 so that the edges of the openings can be secured with sutures (not shown) to the support member. During delivery and implantation of the apparatus 300, care must be taken to ensure that the openings 290 align with the coronary ostiums 284 and 286. If a percutaneous approach is being used, additional radiopaque markers can be placed around the openings 290 to guide proper placement of the apparatus 300.

The apparatus 300 according to the embodiment of FIGS. 19 and 20 is implanted in the same manner as described above for the apparatus 200 and performs the same functions as the apparatus 200. Further, the apparatus 300 enjoys all of the benefits and advantages discussed above with regard to the apparatus 200, including resisting thrombosis and platelet deposition, remodeling the profile of a dilatated native valve to a predetermined memorized shape and size, preventing prolapse of the leaflets 204 and 206, providing long term durability, and avoiding an open surgical procedure by being percutaneously deliverable to the heart.

Figure 21:
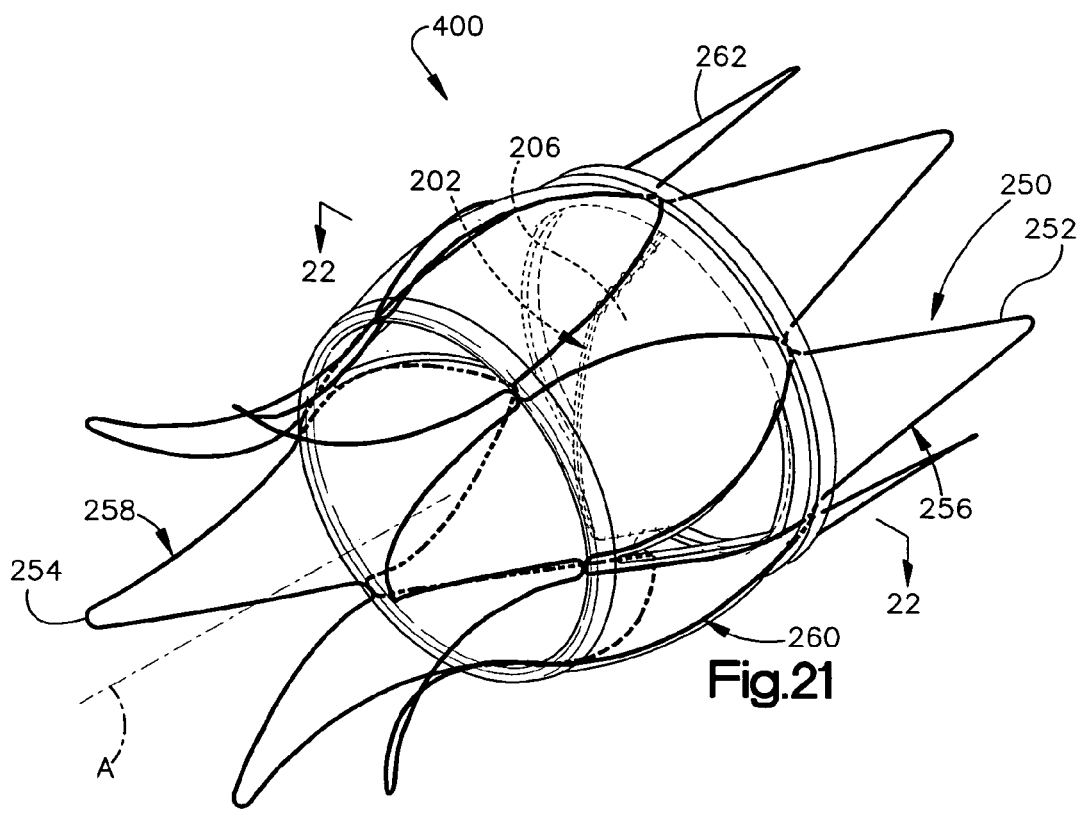
FIG. 21 is a perspective view of a twelfth embodiment of an apparatus constructed in accordance with the present invention.
Figure 22:
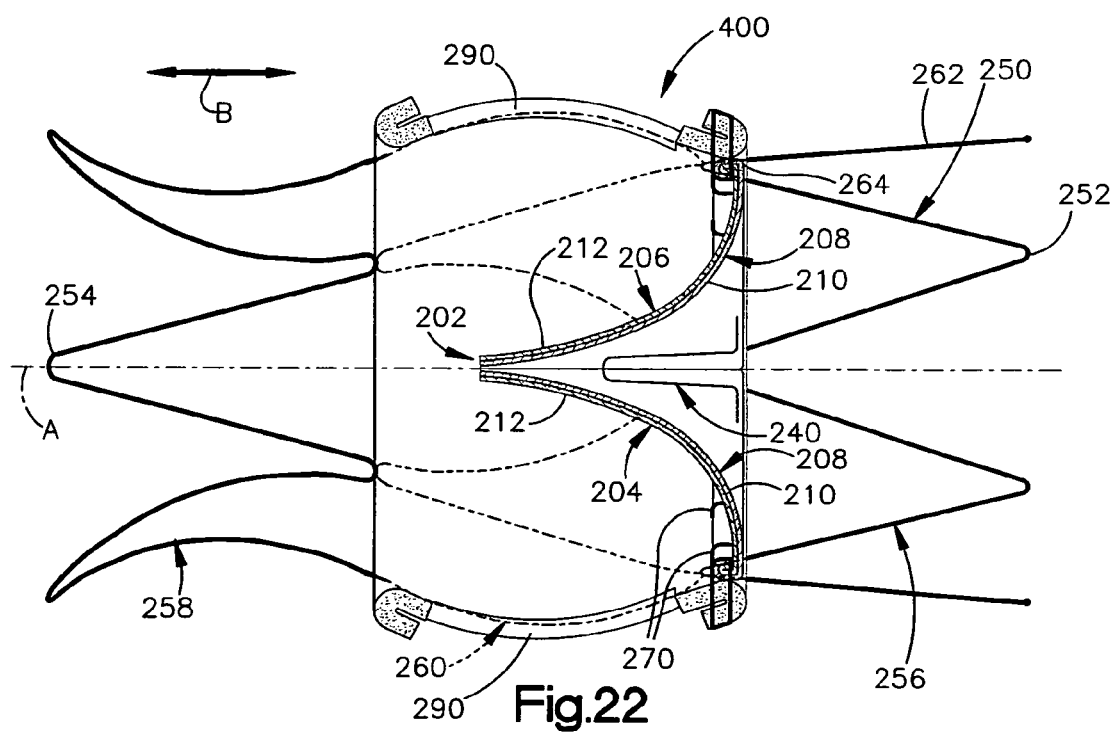
FIG. 22 is a section view taken along line 22-22 in FIG. 21.

FIGS. 21 and 22 illustrate an apparatus 400 constructed in accordance with a twelfth embodiment of the present invention. In the twelfth embodiment of FIGS. 21 and 22, structures of the twelfth embodiment that are the same as structures described in the previous embodiments have the same reference numbers.

The difference between the apparatus 400 and the previously described apparatus 300 is that the layer of biological material 14a extends only through the center section 260 of the support member 250. The layer of biological material 14a thus extends along, and is attached to, the inner surface 264 of the support member 250 in the center section 260. Thus, in the twelfth embodiment of the present invention, the proximal end section 256 of the support member 250 is a bare stent section. As with the previous embodiment, care must be taken during delivery and placement of the apparatus 400 to ensure that the openings 290 align with the coronary ostiums 284 and 286.

The apparatus 400 according to the embodiment of FIGS. 21 and 22 is implanted in the same manner as described above for the apparatus 200 and performs the same functions as the apparatus 200. Further, the apparatus 400 enjoys all of the benefits and advantages discussed above with regard to the apparatus 200, including resisting thrombosis and platelet deposition, remodeling the profile of a dilatated native valve to a predetermined memorized shape and size, preventing prolapse of the leaflets 204 and 206, providing long term durability, and avoiding an open surgical procedure by being percutaneously deliverable to the heart.

It should be understood by those skilled in the art that the apparatus 200/300/400 described above could be adapted to replace any of the other three cardiac valves, could be positioned in the superior vena cava or the inferior vena cava at their respective entrances to the right atrium, and could also be used in a blood vessel as a venous valve. Implantation of the apparatus 200/300/400 in any of these additional locations could be accomplished through either an open surgical procedure or a percutaneous intravascular approach.

From the above description of the invention, those skilled in the art will perceive improvements, changes and modifications. For example, it is contemplated that known drug-eluting technologies could be incorporated into the apparatuses of the present invention. It is further contemplated that cell-seeding technology could be employed to improve the bonding of the biological tissue 14a to the native tissue and reduce the chance of antigenicity. Such improvements, changes and modifications within the skill of the art are intended to be covered by the appended claims.

We claim:

1. A prosthetic valve for replacing a cardiac valve, said prosthetic valve comprising:
    an expandable support member comprising a stent having inner and outer surfaces;
    at least two valve leaflets made of a first layer of biological material selected from a group consisting of peritoneal tissue, pleural tissue, and pericardial tissue;
    said stent having oppositely disposed proximal and distal end sections and a center section disposed between said end sections, said at least two valve leaflets extending within said center section;
    a second layer of biological material attached to said support member, said second layer being selected from a group consisting of peritoneal tissue, pleural tissue, and pericardial tissue, said second layer being attached to said inner surface;
    said second layer including a radially inwardly facing surface that defines a conduit for directing blood flow;
    said at least two valve leaflets extending across said conduit to permit unidirectional flow of blood through said conduit; and
    wherein said center section of said stent has a convex shape in the axial direction for conforming to the shape of the cardiac wall downstream of the cardiac valve.

2. The prosthetic valve of claim 1 wherein said distal end section of said stent has a concave shape in the axial direction for conforming to the shape of the cardiac wall downstream of the cardiac valve.

3. A prosthetic valve for replacing a cardiac valve, said prosthetic valve comprising:
    an expandable support member comprising a stent having inner and outer surfaces;
    at least two valve leaflets made of a first layer of biological material selected from a group consisting of peritoneal tissue, pleural tissue, and pericardial tissue;
    said stent having oppositely disposed proximal and distal end sections and a center section disposed between said end sections, said at least two valve leaflets extending within said center section;
    a second layer of biological material attached to said support member, said second layer being selected from a group consisting of peritoneal tissue, pleural tissue, and pericardial tissue, said second layer being attached to said inner surface;
    said second layer including a radially inwardly facing surface that defines a conduit for directing blood flow;
    said at least two valve leaflets extending across said conduit to permit unidirectional flow of blood through said conduit; and
    wherein at least one of said proximal, distal, and center sections of said stent is balloon-expanded; at least one of said proximal, distal, and center sections of said stent is self-expanding; and said proximal section of said stent is balloon-expanded and said distal and center sections are self-expanding.

4. A prosthetic valve for replacing an aortic valve, said prosthetic valve comprising:
    an expandable stent having inner and outer surfaces, said stent having oppositely disposed proximal and distal end sections and a center section disposed between said end sections;
    at least two valve leaflets made of a first layer of biological material selected from a group consisting of peritoneal tissue, pleural tissue, and pericardial tissue, said at least two valve leaflets extending within said center section;

a second layer of biological material attached to said inner surface of said stent, said second layer being selected from a group consisting of peritoneal tissue, pleural tissue, and pericardial tissue;

said second layer including a radially inwardly facing surface that defines a conduit for directing blood flow;

said at least two valve leaflets extending across said conduit to permit unidirectional flow of blood through said conduit; and wherein said center section of said stent has a convex shape in the axial direction for conforming to the shape of the cardiac wall downstream of the aortic valve.

5. The prosthetic valve of claim 4 wherein said distal end section of said stent has a concave shape in the axial direction for conforming to the shape of the cardiac wall downstream of the aortic valve.

6. A prosthetic valve for replacing an aortic valve, said prosthetic valve comprising:

an expandable stent having inner and outer surfaces, said stent having oppositely disposed proximal and distal end sections and a center section disposed between said end sections;

at least two valve leaflets made of a first layer of biological material selected from a group consisting of peritoneal tissue, pleural tissue, and pericardial tissue, said at least two valve leaflets extending within said center section;

a second layer of biological material attached to said inner surface of said stent, said second layer being selected from a group consisting of peritoneal tissue, pleural tissue, and pericardial tissue;

said second layer including a radially inwardly facing surface that defines a conduit for directing blood flow;

said at least two valve leaflets extending across said conduit to permit unidirectional flow of blood through said conduit; and wherein at least one of said proximal, distal, and center sections of said stent is balloon-expanded; at least one of said proximal, distal, and center sections of said stent is self-expanding; and said proximal section of said stent is balloon-expanded and said distal and center sections are self-expanding.

* * * * *